US008129145B2

(12) United States Patent (10) Patent No.: US 8,129,145 B2
Lasko et al. (45) Date of Patent: Mar. 6, 2012

(54) PRODUCTION OF GLYCOPROTEINS

(75) Inventors: Daniel R. Lasko, Medford, MA (US); Stephan M. Koza, Newbury, MA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/827,301

(22) Filed: Jul. 11, 2007

(65) Prior Publication Data

US 2008/0081356 A1 Apr. 3, 2008

Related U.S. Application Data

(60) Provisional application No. 60/830,658, filed on Jul. 13, 2006.

(51) Int. Cl.
*C12P 21/04* (2006.01)
*C07K 14/00* (2006.01)
*C12N 5/06* (2006.01)
(52) U.S. Cl. ........ 435/69.1; 435/404; 530/380; 530/386
(58) Field of Classification Search ................. 435/69.1, 435/404; 530/380, 386
See application file for complete search history.

(56) References Cited

U.S. PATENT DOCUMENTS

| 4,767,704 | A | 8/1988 | Cleveland et al. |
| 5,045,467 | A | 9/1991 | Bertheussen |
| 5,122,469 | A | 6/1992 | Mather et al. |
| 5,156,964 | A | 10/1992 | Inlow et al. |
| 5,316,938 | A | 5/1994 | Keen et al. |
| 6,048,728 | A | 4/2000 | Inlow et al. |
| 6,506,598 | B1 | 1/2003 | Andersen et al. |
| 7,294,484 | B2 | 11/2007 | Drapeau |
| 2004/0001822 | A1* | 1/2004 | Levanon et al. ........... 424/130.1 |

FOREIGN PATENT DOCUMENTS

| EP | 0481791 B1 | 4/1992 |
| EP | 1 096 017 | 5/2001 |
| WO | WO 96/39488 | 12/1996 |
| WO | 0170968 | 9/2001 |
| WO | WO-2004/008100 | 1/2004 |
| WO | WO 2006/026408 | 3/2006 |
| WO | WO 2007/070315 | 6/2007 |

OTHER PUBLICATIONS

Andersen, et al., *Biotechnology and Bioengineering*, 70:25-31, 2000.
Bond, et al., *Seminars in Hematology*, 35:11-17, 1998.
Crowell, et al., *Biotechnology and Bioengineering*, 96:538-549, 2007.
International Search Report, PCT/US/2007/015767, mailed Nov. 20, 2007.
Kaufman, et al., *Biochemistry*, 33:9813-9819, 1994.
Restelli, et al., *Cell Engineering*, 3:61-92, 2002.
Altamirano et al., "Improvement of CHO cell culture medium formulation: Simultaneous substitution of glucose and glutamine," *Biotechnology Progress* 16(1):69-75 (2000).
Baker et al., "Metabolic Control of Recombinant Protein N-Glycan Processing in NS0 and CHO cells," *Biotechnol. Bioeng.* 73:188-202 (2001).
Barnes et al., "Methods for growth of cultured cells in serum-free medium," *Anal Biochem.* 102(2):255-70 (1980).
Barnes et al., "Serum-free cell culture: a unifying approach," *Cell* 22(3):649-55 (1980).
Bertheussen, "Growth of cells in a new defined protein-free medium," *Cytotechnology* 11:219-231 (1993).
Birch et al., "The Choline and Serum Protein Requirements of Mouse Fibroblast Cells (Strain LS) in Culture," *Journal of Cell Science* 5:135-142 (1969).
Breton et al., "Structure/function studies of glycosyltransferases," *Current Opinion in Structural Biology* 9:563-571 (1999).
Brooks, "Appropriate Glycosylation of Recombinant Proteins for Human Use," *Mol Biotechnol.* 28(3):241-55 (2004).
Bruckner et al., "Glycosyltransferase activity of Fringe modulates Notch-Delta interactions," *Nature* 406:411-415 (2000).
Busch et al., "A Common Motif of Eukaryotic Glycosyltransferases Is Essential for the Enzyme Activity of Large Clostridial Cytotoxins," *J Biol Chem.* 273(31):19566-72 (1998).
Hamilton et al., "Clonal Growth of Chinese Hamster Cell Lines in Protein-free Media," In Vitro 13(9): 82-93 (1977).
Jiao et al., "Manganese sulfate-dependent glycosylation of endogenous glycoproteins in human skeletal muscle is catalyzed by a nonglucose 6-P-dependent glycogen synthase and not glycogenin," *Biochim Biophys Acta.* 1427(1):1-12 (1999).
Kaufman et al., "Depletion of manganese within the secretory pathway inhibits O-linked glycosylation in mammalian cells." *Biochemistry* 33(33):9813-9819 (1994).
Keen et al., "Development of a serum-free culture medium for the large scale production of recombinant protein from a Chinese hamster ovary cell line," *Cytotechnology* 17:153-163 (1995).
Kitos et al., "Glutamine metabolism by animal cells growing in a synthetic medium," *Experimental Cell Research* 27:307-316 (1962).
Lifely et al., "Glycosylation and biological activity of CAMPATH-1H expressed in different cell lines and grown under different culture conditions," *Glycobiology.* 5(8):813-22 (1995). Ling et al., "Chemically characterized concentrated corodies for continuous cell culture (the 7C's culture media)," *Experimental Cell Research* 52:469-489 (1968).
Moloney et al. "Mammalian Notch1 is modified with two unusual forms of O-linked glycosylation found on Epidermal Growth Factor-like modules," *Journal of Biological Chemistry* 275(13):9604-9611 (2000).
McLawhon et al., "Glycosylation-Dependent Regulation of Opiate (Enkephalin) Receptors in Neurotumor Cells," *J Neurochem.* 41(5):1286-96 (1983).
Merello et al., "Characterization and Partial Purification of a Novel Enzymatic Activity UDP-GlcNAc:Ser-Protein N-Acetylglucosamine-1-Phosphotransferase from the Cellular Slime Mold Dictyostelium Discoideum," *J Biol Chem.* 270(13):7281-7287 (1995).

(Continued)

*Primary Examiner* — Chih-Min Kam
(74) *Attorney, Agent, or Firm* — Pfizer Inc.

(57) ABSTRACT

An improved system for large scale production of glycoproteins in cell culture is provided. In accordance with the present invention, cells expressing a glycoprotein are grown in media that contain manganese at a concentration of between approximately 10 and 600 nM. The use of such a system allows production of a glycoprotein with an increased glycosylation pattern and/or a glycosylation pattern that more accurately reflects the glycosylation pattern of the naturally occurring glycoprotein. A glycoprotein expressed in accordance with the present invention may be advantageously used in the preparation of pharmaceutical compositions.

18 Claims, 4 Drawing Sheets

OTHER PUBLICATIONS

Moloney et al., "The O-linked fucose glycosylation pathway: identification and characterization of a uridine diphosphoglucose: fucose-β1,3-glucosyltransferase activity from Chinese hamster ovary cells," *Glycobiology* 9(7):679-87 (1999).

Ross et al., "Partial characterization of galactosyltransferase in human seminal plasma and its distribution in the human epididymis," *J Reprod Fertil.* 98(1):129-37 (1993).

Sarubbi et al., "The differential glycosylation of human pro-urokinase from various recombinant mammalian cell lines does not affect activity and binding to PAI-1," *Thromb Haemost.* 62(3):927-33 (1989).

Shao et al., "O-Glycosylation of EGF repeats: identification and initial characterization of a UDP-glucose: protein O-glucosyltransferase," *Glycobiology* 12(11):763-70 (2002).

Spaargaren, "The design of culture media based on the elemental composition of biological material," *J Biotechnol.* 45:97-102 (1996).

Tarbouriech et al, "Three-dimensional Structures of the Mn and Mg dTDP Complexes of the Family GT-2 Glycosyltransferase SpsA: A Comparison with Related NDP-sugar Glycosyltransferases," *J Mol Biol.* 314(4):655-61 (2001).

Wiggins et al., "Activity of the yeast MNN1 α-1,3-mannosyltransferase requires a motif conserved in many other families of glycosyltransferases," *Proc Natl Aced Sci USA* 95(14):7945-50 (1998).

Yang et al., "Effects of Ammonia and Glucosamine on the Heterogeneity of Erythropoietin Glycoforms," *Biotechnol. Prog.* 18:129-138 (2002).

International Search Report, PCT/US2007/015767, date of mailing Nov. 20, 2007.

Written Opinion, PCT/US2007/015767, date of mailing Nov. 20, 2007.

* cited by examiner

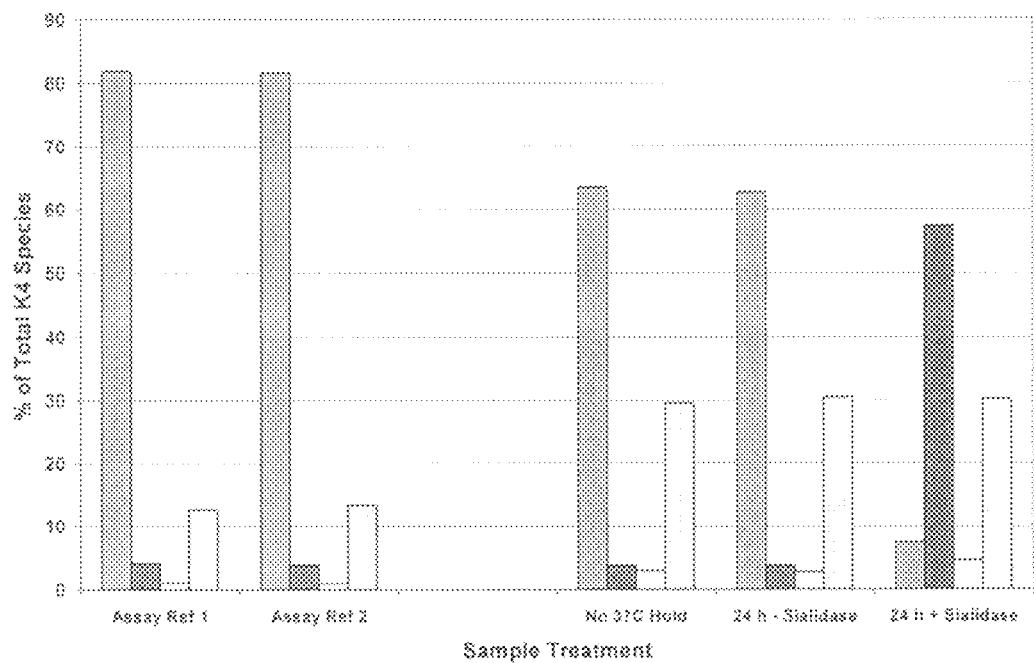
Figure 1. Investigation of Glycosidic Activity in UF/DF Retentate Material.
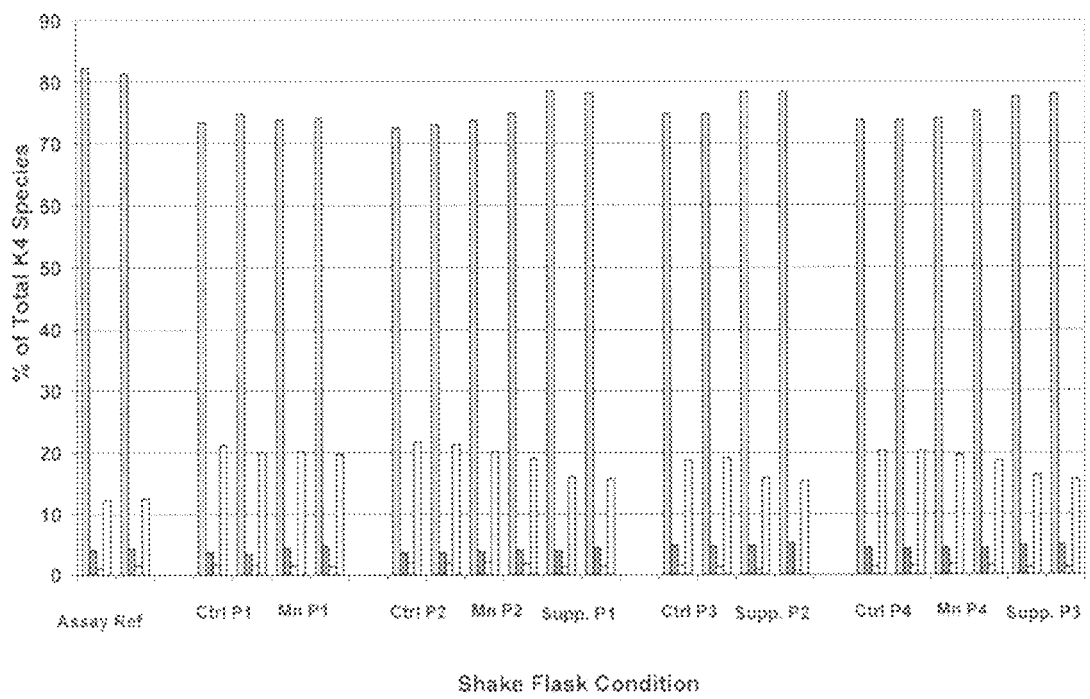
Figure 2. K4 Species Distributions in rFIX Generated in Shake Flask Cultures.

Figure 3. K4 Species Distributions from Shake Flask Cultures with Various Media Additives.
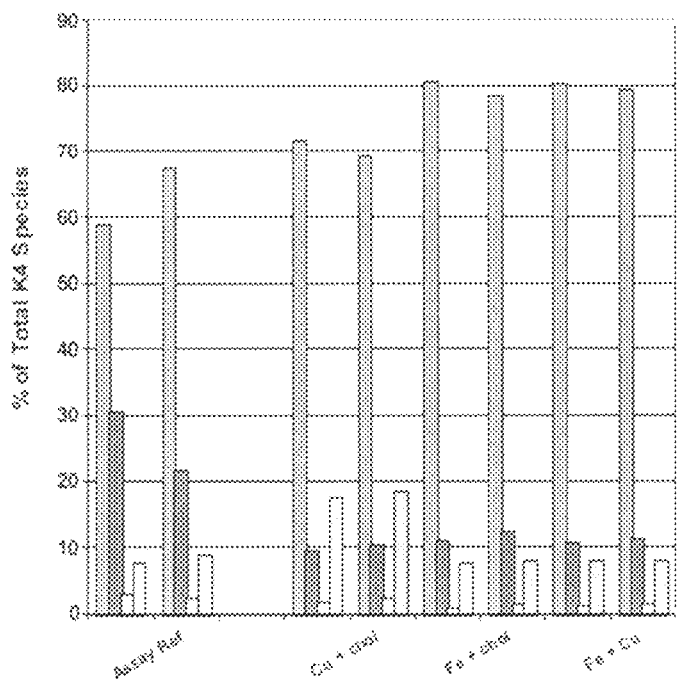
Figure 4. K4 Species Distribution of Shake Flask Cultures with supplemented PTR Medium.
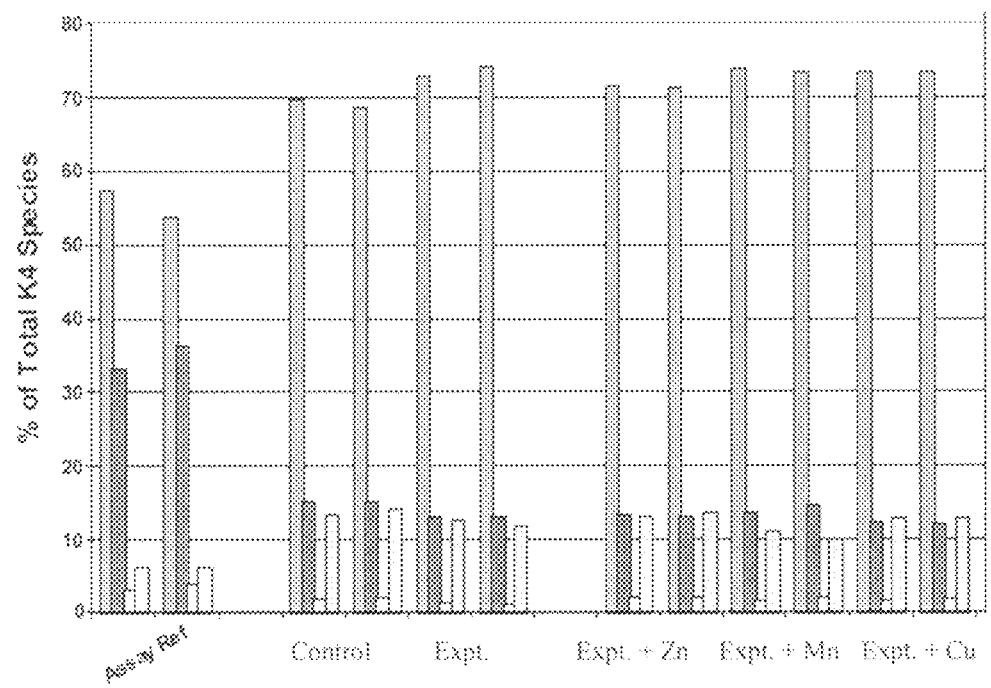

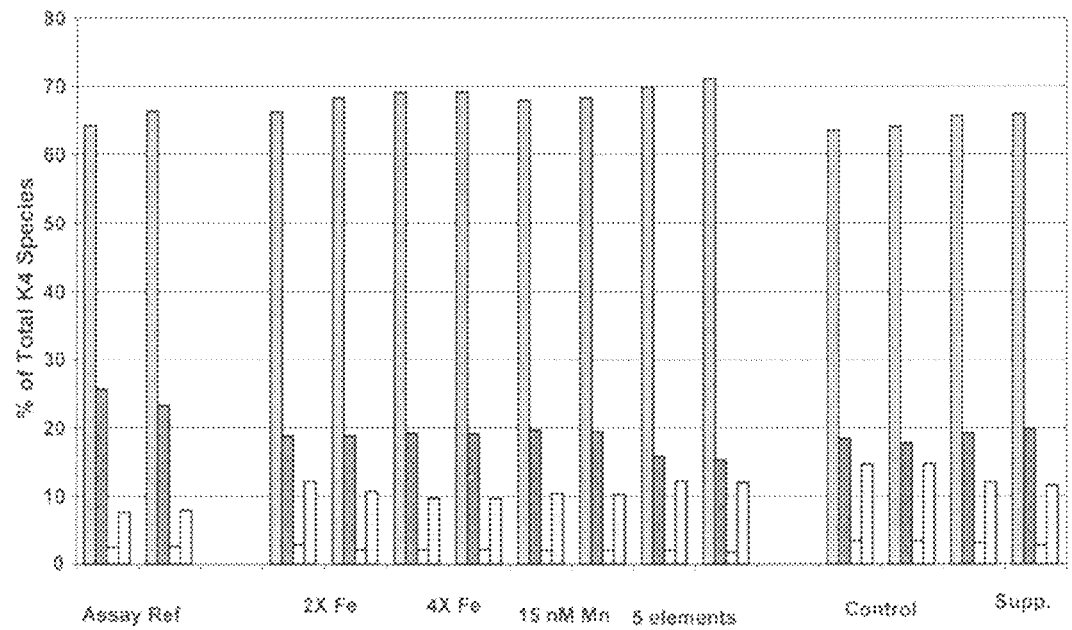
Figure 5. K4 Species Distributions from Shake Flask Cultures with Various Medium Additives.
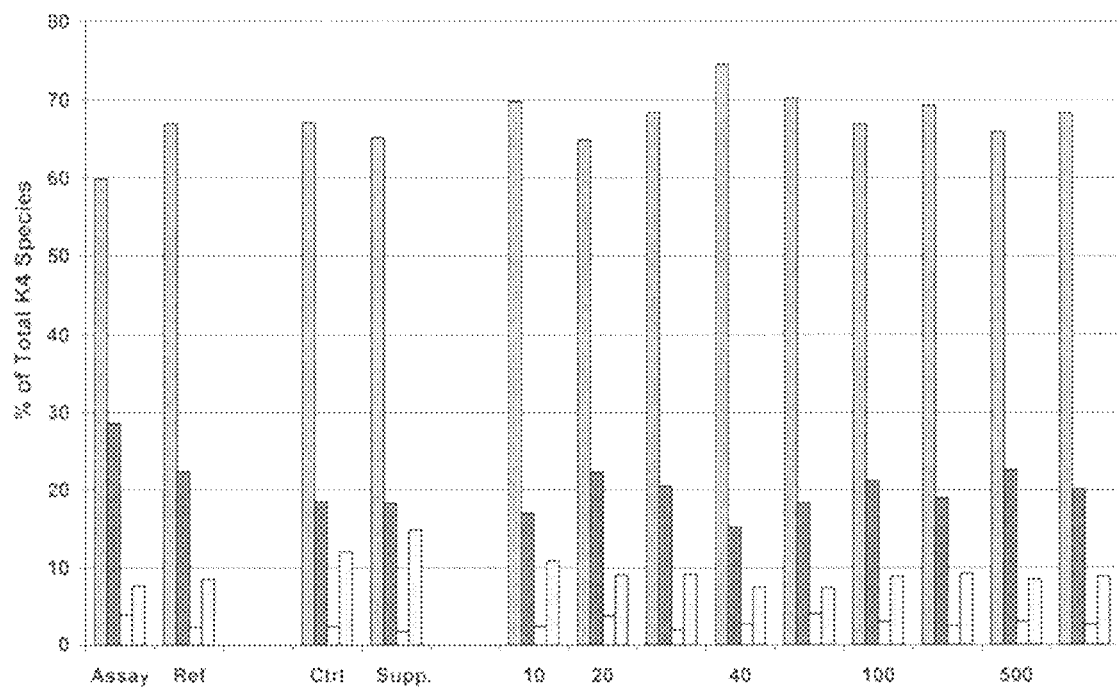
Figure 6. K4 Species Distributions from Shake Flask Cultures at Varying Manganese Levels.

Figure 7. Graphical Comparison of Percentage of Total Peak Area for G0, G1, and G2 HPAEC-PED Peaks.
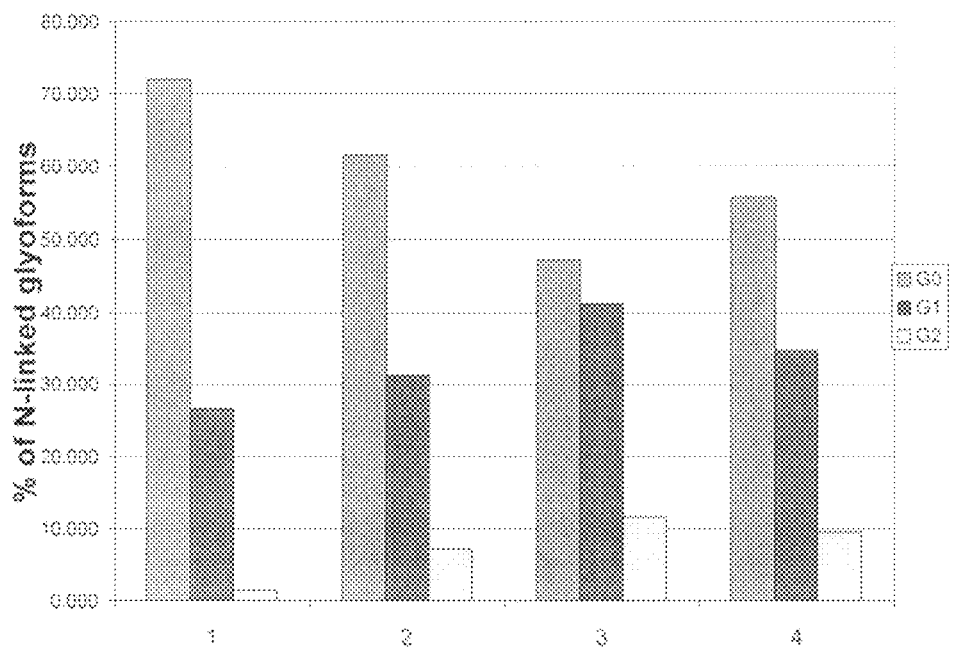
Figure 8. Graphical Comparison of Percentage of Total Peak Area for G0, G1, and G2 HPAEC-PED Peaks.
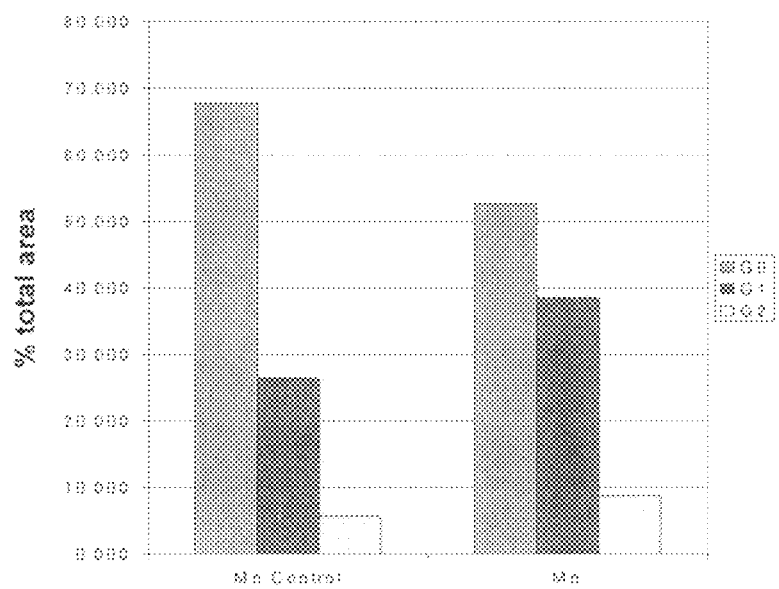

PRODUCTION OF GLYCOPROTEINS

CROSS-REFERENCE TO RELATED APPLICATIONS

This application is co-pending with, shares at least one common inventor with, and claims priority to U.S. Provisional Patent Application No. 60/830,658, filed Jul. 13, 2006, the contents of which are hereby incorporated by reference in their entirety.

BACKGROUND OF THE INVENTION

Proteins and polypeptides have become increasingly important therapeutic agents. In most cases, these proteins and polypeptides are produced in cell culture, from cells that have been engineered and/or selected to produce unusually high levels of the particular protein or polypeptide of interest. Control and optimization of cell culture conditions is critically important for successful commercial production of proteins and polypeptides.

Many proteins and polypeptides produced in cell culture are glycoproteins that contain covalently linked carbohydrate structures including oligosaccharide chains. These oligosaccharide chains are linked to the protein in the endoplasmic reticulum and the Golgi apparatus via either N-linkages or O-linkages. The oligosaccharide chains may comprise a significant portion of the mass of the glycoprotein. The oligosaccharide chains are thought to play key roles in the function of the glycoprotein including facilitating correct folding of the glycoprotein, mediating protein-protein interactions, conferring stability, conferring advantageous pharmacodynamic and/or pharmacokinetic properties, inhibiting proteolytic digestion, targeting the glycoprotein to the proper secretory pathway and targeting the glycoprotein to a particular organ or organs.

Generally, N-linked oligosaccharide chains are added to the nascent, translocating protein in the lumen of the endoplasmic reticulum (see Molecular Biology of the Cell, by Alberts et al., 1994, incorporated herein by reference). The oligosaccharide is added to the amino group on the side chain of an asparagine residue contained within the target consensus sequence of Asn-X-Ser/Thr, where X may be any amino acid except proline. The initial oligosaccharide chain is usually trimmed by specific glycosidase enzymes in the endoplasmic reticulum, resulting in a short, branched core oligosaccharide composed of two N-acetylglucosamine and three mannose residues.

After initial processing in the endoplasmic reticulum, the glycoprotein is shuttled via small vesicles to the Golgi apparatus, where the oligosaccharide chain undergoes further processing before being secreted to the cell surface. The trimmed N-linked oligosaccharide chain may be modified by the addition of several mannose residues, resulting in a high-mannose oligosaccharide. Alternatively, one or more monosaccharides units of N-acetylglucosamine may be added to the core mannose subunits to form complex oligosaccharides. Galactose may be added to the N-acetylglucosamine subunits, and sialic acid subunits may be added to the galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases.

In addition to being modified by the N-linked glycosylation pathway, glycoproteins may also be modified by the addition of O-linked oligosaccharide chains to specific serine or threonine residues as they are processed in the Golgi apparatus. The residues of an O-linked oligosaccharide are added one at a time and the addition of each residue is catalyzed by a specific enzyme. In contrast to N-linked glycosylation, the consensus amino acid sequence for O-linked glycosylation is less well defined.

The ultimate quality and extent of protein glycosylation can be dramatically affected by the conditions of the cell culture. For example, traditional batch and fed-batch culture processes have focused on the ultimate level of the peptide produced and often result in production of a glycoprotein with a less extensive glycosylation pattern and/or a glycosylation pattern whose sugar residues of the oligosaccharide chains poorly reflect the sugar residues that are present in the naturally occurring form of the glycoprotein. Increasing the extent of glycosylation and/or adjusting the composition of the sugar residues to more closely reflect the level and composition of glycosylation that are present in the natural form of the glycoprotein could potentially result in a therapeutic glycoprotein agent with greater potency, improved pharmacodynamic and/or pharmacokinetic properties and fewer side effects. While some effort has been made to improve the quality and quantity of glycosylation of glycoproteins produced in cell culture, there remains a need for additional improvements. There is a particular need for the development of systems for producing glycoproteins with improved glycosylation patterns by cell culture in defined media.

SUMMARY OF THE INVENTION

Methods and compositions of the present invention provide an improved system for large scale production of glycoproteins with improved glycosylation patterns in cell culture. For example, in certain embodiments, the present invention provides commercial scale (e.g., 500 L or more) culture methods that utilize a medium containing a molar cumulative concentration of manganese between approximately 10 and 600 nM. In certain embodiments, the molar cumulative glutamine concentration in the media is less than approximately 8 mM. In certain embodiments, the molar cumulative glutamine concentration in the media is less than approximately 4 mM. It should be understood that "cumulative", as used above, refers to the total amount of a particular component or components added over the course of the cell culture, including components added at the beginning of the culture and subsequently added components. In certain embodiments of the invention, it is desirable to minimize "feeds" of the culture over time, so that it is desirable to maximize amounts present initially. Of course, medium components are metabolized during culture so that cultures with the same cumulative amounts of given components will have different absolute levels if those components are added at different times (e.g. all present initially vs. some added by feeds).

According to the present invention, use of such a medium allows production of glycoproteins that contain desirable glycosylation patterns. In some embodiments, the glycoproteins may have a more extensive glycosylation pattern and/or may have a distribution of oligosaccharide chains that more closely resembles the distribution of oligosaccharide chains applied to the glycoprotein by the natural host cell. In some embodiments, use of the inventive system may result in production of a glycoprotein with a glycosylation pattern similar or identical to the glycosylation pattern that would be present if the glycoprotein were expressed in an endogenous human cell.

One of ordinary skill in the art will understand that media formulations of the present invention encompass both defined and complex media. In certain embodiments, the culture medium is a defined medium in which the composition of the medium is known and controlled.

In some embodiments, the cells are grown under one or more of the conditions described in U.S. Provisional Patent Application Ser. No. 60/605,097, incorporated herein by reference. In some embodiments, the cells are grown under one or more of the conditions described in U.S. patent application Ser. No. 11/213,308, incorporated herein by reference.

Cell cultures of the present invention may optionally be supplemented with nutrients and/or other medium components including hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source. In certain embodiments, it may be beneficial to supplement the media with chemical inductants such as hexamethylene-bis(acetamide) ("HMBA") and sodium butyrate ("NaB"). Such optional supplements may be added at the beginning of the culture or may be added at a later point in order to replenish depleted nutrients or for another reason. In general, it is desirable to select the initial medium composition to minimize supplementation in accordance with the present invention.

BRIEF DESCRIPTION OF THE DRAWING

FIG. 1 shows Investigation of Glycosidic Activity in UF/DF Retentate Material. For each experiment, the bars representing the various K4 and K4' species are, from left to right: K4 (Fuc-GlcNAc-Gal-SA), K4' (Fuc-GlcNAc-Gal), K4' (Fuc-GlcNAc) and K4' (Fuc).

FIG. 2 shows K4 Species Distributions in rFIX Generated in Shake Flask Cultures. For each experiment, the bars representing the various K4 and K4' species are, from left to right: K4 (Fuc-GlcNAc-Gal-SA), K4' (Fuc-GlcNAc-Gal), K4' (Fuc-GlcNAc) and K4' (Fuc).

FIG. 3 shows K4 Species Distributions from Shake Flask Cultures with Various Media Additives. For each experiment, the bars representing the various K4 and K4' species are, from left to right: K4 (Fuc-GlcNAc-Gal-SA), K4' (Fuc-GlcNAc-Gal), K4' (Fuc-GlcNAc) and K4' (Fuc).

FIG. 4 shows K4 Species Distribution of Shake Flask Cultures with Supplemented Medium. For each experiment, the bars representing the various K4 and K4' species are, from left to right: K4 (Fuc-GlcNAc-Gal-SA), K4' (Fuc-GlcNAc-Gal), K4' (Fuc-GlcNAc) and K4' (Fuc).

FIG. 5 shows K4 Species Distributions from Shake Flask Cultures with Various Medium Additives. For each experiment, the bars representing the various K4 and K4' species are, from left to right: K4 (Fuc-GlcNAc-Gal-SA), K4' (Fuc-GlcNAc-Gal), K4' (Fuc-GlcNAc) and K4' (Fuc).

FIG. 6 shows K4 Species Distributions from Shake Flask Cultures at Varying Manganese Levels. For each experiment, the bars representing the various K4 and K4' species are, from left to right: K4 (Fuc-GlcNAc-Gal-SA), K4' (Fuc-GlcNAc-Gal), K4' (Fuc-GlcNAc) and K4' (Fuc).

FIG. 7 shows a Graphical Comparison of Percentage of Total Peak Area for G0, G1, and G2 HPAEC-PED Peaks. For each experiment, the bars representing the complex N-linked biantennary glycans are, from left to right: G0, G1 and G2.

FIG. 8 shows a Graphical Comparison of Percentage of Total Peak Area for G0, G1 and G2 HPAEC-PED Peaks. For each experiment, the bars representing the complex N-linked biantennary glycans are, from left to right: G0, G1 and G2.

DEFINITIONS

"Amino acid": The term "amino acid" as used herein refers to any of the twenty naturally occurring amino acids that are normally used in the formation of polypeptides, or analogs or derivatives of those amino acids or any non-naturally occurring amino acid. Amino acids of the present invention are provided in medium to cell cultures. Amino acids provided in the medium may be provided as salts or in hydrate form.

"Antibody": The term "antibody" as used herein refers to an immunoglobulin molecule or an immunologically active portion of an immunoglobulin molecule, i.e., a molecule that contains an antigen binding site which specifically binds an antigen, such as a Fab or F(ab')$_2$ fragment. In certain embodiments, an antibody is a typical natural antibody known to those of ordinary skill in the art, e.g., glycoprotein comprising four polypeptide chains: two heavy chains and two light chains. In certain embodiments, an antibody is a single-chain antibody. For example, in some embodiments, a single-chain antibody comprises a variant of a typical natural antibody wherein two or more members of the heavy and/or light chains have been covalently linked, e.g., through a peptide bond. In certain embodiments, a single-chain antibody is a protein having a two-polypeptide chain structure consisting of a heavy and a light chain, which chains are stabilized, for example, by interchain peptide linkers, which protein has the ability to specifically bind an antigen. In certain embodiments, an antibody is an antibody comprised only of heavy chains such as, for example, those found naturally in members of the Camelidae family, including llamas and camels (see, for example, U.S. Pat. Nos. 6,765,087 by Casterman et al., 6,015,695 by Casterman et al., 6,005,079 and by Casterman et al., each of which is incorporated by reference in its entirety). The terms "monoclonal antibodies" and "monoclonal antibody composition", as used herein, refer to a population of antibody molecules that contain only one species of an antigen binding site and therefore usually interact with only a single epitope or a particular antigen. Monoclonal antibody compositions thus typically display a single binding affinity for a particular epitope with which they immunoreact. The terms "polyclonal antibodies" and "polyclonal antibody composition" refer to populations of antibody molecules that contain multiple species of antigen binding sites that interact with a particular antigen.

"Batch culture": The term "batch culture" as used herein refers to a method of culturing cells in which all the components that will ultimately be used in culturing the cells, including the medium (see definition of "Medium" below) as well as the cells themselves, are provided at the beginning of the culturing process. A batch culture is typically stopped at some point and the cells and/or components in the medium are harvested and optionally purified.

"Bioreactor": The term "bioreactor" as used herein refers to any vessel used for the growth of a mammalian cell culture. A bioreactor can be of any size so long as it is useful for the culturing of mammalian cells. Typically, such a bioreactor will be at least 1 liter and may be 10, 100, 250, 500, 1000, 2500, 5000, 8000, 10,000, 12,000 liters or more, or any volume in between. The internal conditions of the bioreactor, including, but not limited to pH, dissolved oxygen and temperature, are typically controlled during the culturing period. A bioreactor can be composed of any material that is suitable for holding mammalian cell cultures suspended in media under the culture conditions of the present invention, including glass, plastic or metal. The term "production bioreactor" as used herein refers to the final bioreactor used in the production of the glycoprotein of interest. The volume of the production bioreactor is typically at least 500 liters and may be 1000, 2500, 5000, 8000, 10,000, 12,000 liters or more, or any volume in between. One of ordinary skill in the art will be aware of and will be able to choose suitable bioreactors for use in practicing the present invention.

"Cell density": The term "cell density" as used herein refers to the number of cells present in a given volume of medium.

"Cell viability": The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

"Complex medium": The term "complex medium" as used herein refers to a medium that contains at least one component whose identity or quantity is either unknown or uncontrolled.

"Culture", "Cell culture": These terms as used herein refer to a cell population that is suspended in a medium (see definition of "Medium" below) under conditions suitable to survival and/or growth of the cell population. As will be clear to those of ordinary skill in the art, in certain embodiments, these terms as used herein refer to the combination comprising the cell population and the medium in which the population is suspended. In certain embodiments, the cells of the cell culture comprise mammalian cells.

"Defined medium": The term "defined medium" as used herein refers to a medium in which the composition of the medium is both known and controlled.

"Fed-batch culture": The term "fed-batch culture" as used herein refers to a method of culturing cells in which additional components are provided to the culture at a time or times subsequent to the beginning of the culture process. Such provided components typically comprise nutritional components for the cells which have been depleted during the culturing process. Additionally or alternatively, such additional components may include supplementary components (see definition of "Supplementary components" below). In certain embodiments, additional components are provided in a feed medium (see definition of "Feed medium" below). A fed-batch culture is typically stopped at some point and the cells and/or components in the medium are harvested and optionally purified.

"Feed medium": The term "feed medium" as used herein refers to a solution containing nutrients which nourish growing mammalian cells that is added after the beginning of the cell culture. A feed medium may contain components identical to those provided in the initial cell culture medium. Alternatively, a feed medium may contain one or more additional components beyond those provided in the initial cell culture medium. Additionally or alternatively, a feed medium may lack one or more components that were provided in the initial cell culture medium. In certain embodiments, one or more components of a feed medium are provided at concentrations or levels identical or similar to the concentrations or levels at which those components were provided in the initial cell culture medium. In certain embodiments, one or more components of a feed medium are provided at concentrations or levels different than the concentrations or levels at which those components were provided in the initial cell culture medium. Exemplary feed media are shown in Table 2, although the present invention is not limited to the use of these media. One of ordinary skill in the art will recognize that alternative feed media may be used and/or certain alterations may be made to the compositions of the exemplary feed media listed in Table 2. In certain embodiments, a feed medium contains supplementary components (see definition of "Supplementary components" below).

"Fragment": The term "fragment" as used herein refers to a polypeptide that is defined as any discrete portion of a given polypeptide that is unique to or characteristic of that polypeptide. For example, the term as used herein refers to any portion of a given polypeptide that includes at least an established sequence element found in the full-length polypeptide. In certain fragments, the sequence element spans at least 4-5, 10, 15, 20, 25, 30, 35, 40, 45, 50 or more amino acids of the full-length polypeptide. Alternatively or additionally, the term as used herein refers to any discrete portion of a given polypeptide that retains at least a fraction of at least one activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fragment retains 100% of more of the activity of the full-length polypeptide. In certain embodiments, a fragment of the present invention contains a peptide sequence that serves as a glycosylation site. In some embodiments, a fragment of the present invention contains a portion of a glycosylation site such that, when linked to another fragment that contains the other portion of the glycosylation site, a functional glycosylation site is reconstituted.

"Gene": The term "gene" as used herein refers to any nucleotide sequence, DNA or RNA, at least some portion of which encodes a discrete final product, typically, but not limited to, a polypeptide, which functions in some aspect of cellular metabolism or development. Optionally, the gene comprises not only the coding sequence that encodes the polypeptide or other discrete final product, but also comprises regions preceding and/or following the coding sequence that modulate the basal level of expression (see definition of "Genetic control element" below), and/or intervening sequences ("introns") between individual coding segments ("exons").

"Genetic control element": The term "genetic control element" as used herein refers to any sequence element that modulates the expression of a gene to which it is operably linked. Genetic control elements may function by either increasing or decreasing the expression levels and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

"Glycoprotein": The term "glycoprotein" as used herein refers to a protein or polypeptide that contains one or more covalently linked oligosaccharide chains. The oligosaccharide chains may be composed of a single sugar residue, a single unbranched chain of sugar residues or may be composed of a chain of sugar residues that branches one or more times. In certain embodiments, oligosaccharide chains are N-linked. In certain embodiments, oligosaccharide chains are O-linked.

"Glycosylation pattern": The term "glycosylation pattern" refers to the observed glycosylation of a given glycoprotein or glycoproteins. A glycoprotein with a greater number of covalently linked sugar residues in the oligosaccharide chain is said to have an increased or more extensive glycosylation pattern. Conversely, a glycoprotein with fewer covalently linked sugar residues in the oligosaccharide chain is said to have a decreased or less extensive glycosylation pattern. The term "glycosylation pattern" as used herein also refers to a characteristic distribution of several different glycosylation patterns on individual glycoproteins expressed according to the teachings of the present invention. In this sense, an increased glycosylation pattern means an increase in the characteristic distribution of glycosylation patterns of the expressed glycoproteins.

"Host cell": The term "host cell" as used herein refers to a cell that is manipulated according to the present invention to produce a glycoprotein with a desirable glycosylation pattern as described herein. In some embodiments, a host cell is a mammalian cell.

"Hybridoma": The term "hybridoma" as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, pig, goat, and human. In certain embodiments, a hybridoma is a trioma cell line, which results when progeny of heterohybrid myeloma fusions, which are the product of a fusion between human cells and a murine myeloma cell line, are subsequently fused with a plasma cell. In certain embodiments, a hybridoma is any immortalized hybrid cell line that produces antibodies such as, for example, quadromas (See, e.g., Milstein et al., Nature, 537:3053, 1983).

"Medium", "Cell culture medium", "Culture medium": These terms as used herein refer to a solution containing nutrients which nourish growing mammalian cells. Typically, such solutions provide essential and non-essential amino acids, vitamins, energy sources, lipids, and trace elements required by the cell for minimal growth and/or survival. Such a solution may also contain supplementary components (see definition of "Supplementary components" below) that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, a medium is advantageously formulated to a pH and salt concentration optimal for cell survival and proliferation. Exemplary culture media are shown in Table 1, although the present invention is not limited to the use of these media. One of ordinary skill in the art will recognize that alternative culture media may be used and/or certain alterations may be made to the compositions of the exemplary culture media listed in Table 1. In certain embodiments, a medium is a feed medium that is added after the beginning of the cell culture (see definition of "Feed medium", above).

"Polypeptide": The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. For example, a polypeptide may be glycosylated (see definition of "glycoprotein" above).

"Protein": The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

"Recombinantly expressed glycoprotein" and "Recombinant glycoprotein": These terms as used herein refer to a glycoprotein expressed from a host cell that has been manipulated by the hand of man to express that glycoprotein. In certain embodiments, a host cell is a mammalian cell. In certain embodiments, such manipulation comprises one or more genetic modifications. For example, mammalian host cells may be genetically modified by the introduction of one or more heterologous genes encoding a glycoprotein to be expressed. The heterologous recombinantly expressed glycoprotein can be identical or similar to glycoproteins that are normally expressed in the mammalian host cell. Heterologous recombinantly expressed glycoprotein can also be foreign to the host cell, i.e. heterologous to glycoproteins normally expressed in the mammalian host cell. In certain embodiments, a heterologous recombinantly expressed glycoprotein is chimeric in that portions of the glycoprotein contain amino acid sequences that are identical or similar to glycoproteins normally expressed in the mammalian host cell, while other portions are foreign to the host cell. Alternatively, a mammalian host cell may be genetically modified by the activation or upregulation of one or more endogenous genes.

"Supplementary components": The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, supplementary components may be added to the initial cell culture. In certain embodiments, supplementary components may be added after the beginning of the cell culture.

"Titer": The term "titer" as used herein refers to the total amount of recombinantly expressed glycoprotein produced by a mammalian cell culture in a given amount of medium volume. Titer is typically expressed in units of milligrams of glycoprotein per milliliter of medium.

DETAILED DESCRIPTION OF CERTAIN EMBODIMENTS

The present invention provides improved systems for the production of glycoproteins in cell culture. In particular, systems are provided that result in production of a glycoprotein that contains a desirable glycosylation pattern. For example, a glycoprotein may have a more extensive glycosylation pattern and/or may have a distribution of oligosaccharide chains that more closely resembles the distribution of oligosaccharide chains applied to the glycoprotein by the natural host cell. In some embodiments, use of inventive systems may result in production of a glycoprotein with a glycosylation pattern similar or identical to the glycosylation pattern that would be present if the glycoprotein were expressed in an endogenous human cell. Certain embodiments of the invention are discussed in detail below. Those of ordinary skill in the art will understand, however, that various modifications to these embodiments are within the scope of the appended claims. It is the claims and equivalents thereof that define the scope of the present invention, which is not and should not be limited to or by this description of certain embodiments.

Media Compositions

A wide variety of mammalian growth media may be used in accordance with the present invention. In certain embodiments, cells may be grown in one of a variety of chemically defined media, wherein the components of the media are both known and controlled. In certain embodiments, cells may be grown in a complex medium, in which not all components of the medium are known and/or controlled.

Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein and/or glycoprotein producing cell cultures.

Defined media typically consist of roughly fifty chemical entities at known concentrations in water. Most of them also contain one or more well-characterized proteins such as insulin, IGF-1, transferrin or BSA, but others require no protein components and so are referred to as protein-free defined media. The chemical components of the media fall into five broad categories: amino acids, vitamins, inorganic salts, trace elements, and a miscellaneous category that defies neat categorization.

The trace elements consist of a variety of inorganic salts included at micromolar or lower levels. The four most commonly included trace elements present in almost all defined media are iron, zinc, selenium and copper. Iron (ferrous or ferric salts) and zinc are typically added to micromolar concentrations, while the others are usually at nanomolar concentrations. The numerous less common trace elements are usually added at nanomolar concentrations.

Manganese is frequently included among the trace elements as a divalent cation ($MnCl_2$ or $MnSO_4$). In early versions of defined media, it was either omitted or included at a high concentration on the order of 1 µM (see, for example, Barnes and Sato, 1980 [Medium DMEM/F12] and Kitos et. al., 1962 [Medium MD 705/1]). In more recently developed defined media, manganese has been commonly included, but at much lower concentrations, for example in the 1-5 nM range (see, for example, Hamilton and Ham, 1977 [Medium MCDB 301] and Cleveland and Erlanger, 1988 [unnamed medium]).

The present invention encompasses the finding that glycoproteins produced by a culture of cells grown in defined media containing manganese concentrations between these extremes contain more extensive glycosylation patterns than they otherwise would if the cells were grown in traditional media, such as those described above. In certain embodiments, manganese is provided in the medium at a concentration of between approximately 10 and 600 nM. In certain embodiments, manganese is provided in the medium at a concentration of between approximately 20 and 100 nM. In certain embodiments, manganese is provided in the medium at a concentration of approximately 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600 nM, or at any range within these concentrations.

The present invention also encompasses the finding that glycoproteins produced by a culture of cells grown in defined media containing relatively low levels of glutamine contain more extensive glycosylation patterns than they otherwise would if the cells were grown in traditional media that contain higher levels of glutamine. In certain embodiments, the initial level of glutamine in the medium is less than or equal to approximately 8 mM. In certain embodiments, the initial level of glutamine in the medium is less than or equal to approximately 4 mM.

One of ordinary skill in the art will be able to choose the exact manganese concentration within these inventive ranges based on the particular attributes of his or her experimental design, including the character of the cells from which the glycoprotein is expressed, the character of the glycoprotein to be produced, and the presence or absence of other components in the medium in which the cells are grown. For example, differences between N-linked and O-linked structures, or differences between particular oligosaccharide structures within each of these broad classes may require different manganese concentrations in the growth medium in order to produce more extensive and/or more natural oligosaccharide chains.

Glycoproteins

Any glycoprotein that is expressible in a host cell may be produced in accordance with the present teachings. A glycoprotein may be expressed from a gene that is endogenous to the host cell, or from a heterologous gene that is introduced into the host cell. A glycoprotein may be one that occurs in nature, or may alternatively have a sequence that was engineered or selected by the hand of man. A glycoprotein to be produced may be assembled from polypeptide fragments that individually occur in nature, at least one of which contains a peptide sequence that serves as a glycosylation site. Alternatively, each polypeptide fragment may have only a portion of a glycosylation site, which site is reconstituted upon assembly of the polypeptide fragments. Additionally or alternatively, the engineered glycoprotein may include one or more fragments that are not naturally occurring, so long as the engineered glycoprotein contains at least one peptide sequence that serves as a glycosylation site.

Glycoproteins that may desirably be expressed in accordance with the present invention will often be selected on the basis of an interesting or useful biological or chemical activity. For example, the present invention may be employed to express any pharmaceutically or commercially relevant enzyme, receptor, antibody, hormone, regulatory factor, antigen, binding agent etc. The following list of glycoproteins that can be produced according to the present invention is merely exemplary in nature, and is not intended to be a limiting recitation. One of ordinary skill in the art will understand that any glycoprotein may be expressed in accordance with the present invention and will be able to select the particular glycoprotein to be produced based on his or her particular needs.

Clotting Factors

Clotting factors have been shown to be effective as pharmaceutical and/or commercial agents. Given the importance of recombinant clotting factors in the treatment of diseases such as Hemophilia, optimizing the glycosylation pattern of recombinantly produced clotting factors in accordance with the present invention is of particular interest. For example, Coagulation Factor IX (Factor IX, or "FIX") is a single-chain glycoprotein whose deficiency results in Hemophilia B, a disorder in which the blood of the sufferer is unable to clot. Thus, any small wound that results in bleeding is potentially a life-threatening event.

FIX is synthesized as a single chain zymogen that can be activated to a two-chain serine protease (Factor IXa) by release of an activation peptide. The catalytic domain of Factor IXa is located in the heavy chain (see Chang et al., *J. Clin. Invest.*, 100:4, 1997, incorporated herein by reference). FIX has multiple glycosylation sites including both N-linked and O-linked carbohydrates. One particular O-linked structure at Serine 61 (Sia-α2,3-Gal-β1,4-GlcNAc-β1,3-Fuc-α1-O-Ser) was once thought unique to FIX but has since found on a few other molecules including the Notch protein in mammals and *Drosophila* (Maloney et al, *Journal of Biol. Chem.*, 275(13), 2000). FIX produced by Chinese Hamster Ovary ("CHO") cells in cell culture exhibits some variability in the Serine 61 oligosaccharide chain. These different glycoforms, and other potential glycoforms, may have different abilities to induce clotting when administered to humans or animals and/or may have different stabilities in the blood, resulting in less effective clotting.

Hemophilia A, which is clinically indistinguishable from Hemophilia B, is caused by a defect in human clotting factor VIII, another glycoprotein that is synthesized as a single chain zymogen and then processed into a two-chain active form. The present invention may also be employed to control or alter the glycosylation pattern of clotting factor VIII in order to modulate its clotting activity. Other glycoprotein clotting factors that can be produced and whose glycosylation pattern can be controlled or altered in accordance with the present invention include for example, but are not limited to, tissue factor and von Willebrands factor.

Antibodies

Antibodies are proteins that have the ability to specifically bind a particular antigen. Given the large number of antibodies currently in use or under investigation as pharmaceutical or other commercial agents, production of antibodies with desirable glycosylation patterns in accordance with the present invention is of particular interest. Furthermore, antibodies with differing glycosylation patterns may be less likely to initiate an immune response in the individual to which they are administered, resulting in a more effective therapeutic regimen. Additionally or alternatively, antibodies with differing glycosylation patterns in their constant regions may exhibit an improved pharmacokinetic or pharmacodynamic effector function. Additionally or alternatively, antibodies with differing glycosylation patterns may be more stable in the cell culture conditions in which they are produced, for example by being more resistant to proteases or other components in the cell culture, such that a higher final titer of antibody is produced.

Any antibody that can be expressed in a host cell may be used in accordance with the teachings of the present disclosure. In some embodiments, an antibody to be expressed is a monoclonal antibody. In certain embodiments, a monoclonal antibody is a chimeric antibody. A chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described (see e.g., Morrison et al., *Proc. Natl. Acad. Sci. U.S.A.* 81, 6851, 1985; Takeda et al., *Nature* 314, 452, 1985, Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B, each of which is incorporated herein by reference).

In some embodiments, a monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the hypervariable region are replaced with residues from a non-human species that confer a desired antigen specificity or affinity. In certain embodiments, a humanized antibody has an amino acid sequence that is 80, 85, 90, 91, 92, 93, 94, 95, 96, 97, 98, 99 percent identical or higher to a human antibody. In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.*, 80, 7308-7312, 1983; Kozbor et al., *Immunology Today*, 4, 7279, 1983; Olsson et al., *Meth. Enzymol.*, 92, 3-16.1982, each of which is incorporated herein by reference). In some embodiments, altered immunoglobulin molecules are made according to the teachings of PCT Publication WO92/06193 or EP 0239400, each of which is incorporated herein by reference in its entirety.

In certain embodiments, an antibody produced according to the teachings of the present disclosure may contain an immunoglobulin constant or Fc region that exhibits an improved glycosylation pattern. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, *Annu. Rev. Immunol* 9:457-92, 1991; Capel et al., Immunomethods 4:25-34, 1994; and de Haas et al., J. Lab. Clin. Med. 126:330-41, 1995, each of which is incorporated herein by reference in its entirety.

As but one non-limiting example, an antibody that may be produced according to the present teachings is an anti-ABeta antibody. Anti-ABeta antibodies are a particularly promising potential avenue of therapy in the treatment of Alzheimer's disease. Alzheimer's disease (AD) is a progressive disease resulting in senile dementia (see generally: Selkoe, TINS 16:403, 1993; Hardy et al., WO 92/13069; Selkoe, J. Neuropathol. Exp. Neurol. 53:438, 1994; Duff et al., Nature 373: 476, 1995; Games et al., Nature 373:523, 1995, each of which is incorporated herein by reference). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 µm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed ABeta or Beta-amyloid peptide. ABeta peptide is a 4-kDa internal fragment of 39-43 amino acids of a larger transmembrane glycoprotein named protein termed amyloid precursor protein (APP). As a result of proteolytic processing of APP by different secretase enzymes, ABeta is primarily found in both a short form, 40 amino acids in length, and a long form, ranging from 42-43 amino acids in length. Part of the hydrophobic transmembrane domain of APP is found at the carboxy end of ABeta, and may account for the ability of ABeta to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease (see, e.g., Goate et al., Nature 349:704, 1991 (valine717 to isoleucine); Chartier Harlan et al. Nature 353:844, 1991 (valine717 to glycine); Murrell et al., Science 254:97, 1991 (valine717 to phenylalanine); Mullan et al., Nature Genet. 1:345, 1992 (a double mutation changing lysine595-methionine596 to asparagine595-leucine596), each of which is incorporated herein by reference in its entirety). Such mutations are thought to cause Alzheimer's disease by increased or altered processing of APP to ABeta, particularly processing of APP to increased amounts of the long form of ABeta (i.e., ABeta1-42 and ABeta1 43). Mutations in other genes, such as the presenilin genes, PS1 and PS2, are thought indirectly to affect processing of APP to generate increased amounts of long form ABeta (see Hardy, TINS 20: 154, 1997, incorporated herein by reference in its entirety).

Mouse models have been used successfully to determine the significance of amyloid plaques in Alzheimer's (Games et al., supra; Johnson-Wood et al., Proc. Natl. Acad. Sci. USA 94:1550, 1997, incorporated herein by reference in its entirety). In particular, when PDAPP transgenic mice, (which express a mutant form of human APP and develop Alzheimer's disease at a young age), are injected with the long form of ABeta, they display both a decrease in the progression of Alzheimer's and an increase in antibody titers to the ABeta peptide (Schenk et al., Nature 400, 173, 1999, incorporated herein by reference in its entirety). The observations discussed above indicate that ABeta, particularly in its long form, is a causative element in Alzheimer's disease.

The ABeta peptide can exist in solution and can be detected in CNS (e.g., CSF) and plasma. Under certain conditions, soluble ABeta is transformed into fibrillary, toxic, Beta-sheet forms found in neuritic plaques and cerebral blood vessels of patients with AD. Treatments involving immunization with monoclonal antibodies against ABeta have been investigated. Both active and passive immunization have been tested as in mouse models of AD. Active immunization resulted in some reduction in plaque load in the brain, but only by nasal administration. Passive immunization of PDAPP transgenic mice has also been investigated (Bard, et al., Nat. Med. 6:916-19, 2000, incorporated herein by reference in its entirety). It was found that antibodies recognizing the amino-terminal and central domains of ABeta stimulated phagocytosis of ABeta deposits, whereas antibodies against domains near the carboxy-terminal domain did not.

The mechanism of clearance of ABeta after passive or active immunization is under continued investigation. Two mechanisms have been proposed for effective clearance, i.e., central degradation and peripheral degradation. The central degradation mechanism relies on antibodies being able to cross the blood-brain barrier, bind to plaques, and induce clearance of pre-existing plaques. Clearance has been shown to be promoted through an Fc-receptor-mediated phagocytosis (Bard, et al., supra). The peripheral degradation mechanism of ABeta clearance relies on a disruption of the dynamic equilibrium of ABeta between brain, CSF, and plasma upon administration of antibody, leading to transport of ABeta from one compartment to another. Centrally derived ABeta is transported into the CSF and the plasma where it is degraded. Recent studies have concluded that soluble and unbound ABeta are involved in the memory impairment associated with AD, even without reduction in amyloid deposition in the brain. Further studies are needed to determine the action and/or interplay of these pathways for ABeta clearance (Dodel, et al., The Lancet Vol. 2:215, 2003, incorporated herein by reference in its entirety).

Anti-ABeta antibodies are a potentially promising route of treatment of AD since they mat bind to and clear the ABeta or other components that comprise the amyloid plaques. Anti-ABeta produced in accordance with the teachings of the present disclosure may serve to better treat Alzheimer's or other related diseases by, for example, binding and clearing components of amyloid plaques more effectively, by clearing amyloid plaques with fewer or less severe side effects, or by preventing formation or build-up of amyloid plaques. In certain embodiments, anti-ABeta antibodies produced in accordance with the present teachings are monoclonal antibodies.

In certain embodiments, anti-ABeta antibodies produced in accordance with the present teachings bind specifically to the aggregated form of ABeta without binding to the soluble form. In certain embodiments, anti-ABeta antibodies produced in accordance with the present teachings bind specifically to the soluble form of anti-ABeta under conditions at which they do not bind to the aggregated form. In certain embodiments, anti-ABeta antibodies produced in accordance with the present teachings bind to both aggregated and soluble forms. In certain embodiments, anti-ABeta antibodies produced in accordance with the present teachings bind ABeta in plaques. In certain embodiments, anti-ABeta antibodies produced in accordance with the present teachings cross the blood-brain barrier. In certain embodiments, anti-ABeta antibodies produced in accordance with the present teachings reduce amyloid burden in a subject. In certain embodiments, anti-ABeta antibodies produced in accordance with the present teachings reduce neuritic dystrophy in a subject. In certain embodiments, anti-ABeta antibodies can maintain synaptic architecture (e.g., synaptophysin).

According to some embodiments, anti-ABeta antibodies produced in accordance with the present teachings bind to an epitope within residues 13-28 of ABeta (with the first N terminal residue of natural ABeta designated 1). In some embodiments, anti-ABeta antibodies produced in accordance with the present teachings bind to an epitope within residues 19-22 of ABeta. In some embodiments, multiple monoclonal antibodies having binding specificities to different anti-ABeta epitopes are used. For example, in some embodiments, an antibody specific for an epitope within residues 19-22 of ABeta is co-administered with an antibody specific for an epitope outside of residues 19-22 of ABeta. Such antibodies can be administered sequentially or simultaneously. Antibodies to amyloid components other than ABeta can also be used (e.g., administered or co-administered).

In certain embodiments, anti-ABeta antibodies produced in accordance with the present teachings bind to an ABeta epitope more strongly or with more specificity than anti-ABeta antibodies otherwise produced. Epitope specificity of an antibody can be determined by known techniques, for example, by forming a phage display library in which different members display different subsequences of ABeta. The phage display library may then be selected for members specifically binding to an antibody under test. A family of sequences is isolated. Typically, such a family contains a common core sequence, and varying lengths of flanking sequences in different members. The shortest core sequence showing specific binding to the antibody typically defines the epitope bound by the antibody. Alternatively or additionally, antibodies may be tested for epitope specificity in a competition assay with an antibody whose epitope specificity has already been determined. For example, antibodies that compete with the 15C11 antibody for binding to ABeta are considered to bind to the same or similar epitope as 15C11, i.e., within residues ABeta 19-22. In certain embodiments, screening antibodies for epitope specificity is a useful predictor of therapeutic efficacy. For example, an antibody determined to bind to an epitope within residues 13-28 (e.g., to Aβ 19-22) of ABeta is likely to be effective in preventing and treating Alzheimer's disease according to the methodologies of the present invention.

Antibodies that specifically bind to a preferred segment of ABeta without binding to other regions of ABeta have a number of advantages relative to monoclonal antibodies binding to other regions, or to polyclonal sera to intact ABeta. Among other things, for equal mass dosages, dosages of antibodies that specifically bind to preferred segments contain a higher molar dosage of antibodies effective in clearing amyloid plaques. Also, antibodies specifically binding to preferred segments may induce a clearing response against amyloid deposits without inducing a clearing response against intact APP polypeptide, thereby reducing the potential side effects.

In certain embodiments, monoclonal, chimeric, single-chain, or humanized antibodies described above may contain amino acid residues that do not naturally occur in any antibody in any species in nature. Such foreign residues can be utilized, for example, to confer novel or modified specificity, affinity or effector function on the monoclonal, chimeric, single-chain or humanized antibody.

Enzymes

Another class of glycoproteins that have been shown to be effective as pharmaceutical and/or commercial agents includes enzymes. Enzymes may be glycoproteins whose glycosylation pattern affects enzymatic activity. Thus, production of enzymes with desirable glycosylation patterns in accordance with the present invention is also of particular interest.

As but one non-limiting example, a deficiency in glucocerebrosidase (GCR) results in a condition known as Gaucher's disease, which is caused by an accumulation of glucocerebrosidase in lysosomes of certain cells. Subjects with Gaucher's disease exhibit a range of symptoms including splenomegaly, hepatomegaly, skeletal disorder, thrombocytopenia and anemia. Friedman and Hayes showed that recombinant GCR (rGCR) containing a single substitution in the primary amino acid sequence exhibited an altered glycosylation pattern, specifically an increase in fucose and N-acetyl glucosamine residues compared to naturally occurring GCR (see U.S. Pat. No. 5,549,892).

Friedman and Hayes also demonstrated that this rGCR exhibited improved pharmacokinetic properties compared to naturally occurring rGCR. For example, approximately twice as much rGCR targeted liver Kupffer cells than did naturally occurring GCR. Although the primary amino acid sequences of the two proteins differed at a single residue, Friedman and Hayes hypothesized that the altered glycosylation pattern of rGCR may also influence the targeting to Kupffer cells.

One of ordinary skill in the art will be aware of other known examples of enzymes that exhibit altered enzymatic, pharmacokinetic and/or pharmacodynamic properties resulting from an alteration in their glycosylation patterns.

Growth Factors and Other Signaling Molecules

Another class of glycoproteins that have been shown to be effective as pharmaceutical and/or commercial agents includes growth factors and other signaling molecules. Thus, production of receptors with desirable glycosylation patterns in accordance with the present invention is also of particular interest. Growth factors are typically glycoproteins that are secreted by cells and bind to and activate receptors on other cells, initiating a metabolic or developmental change in the receptor cell.

Non-limiting examples of mammalian growth factors and other signaling molecules include cytokines; epidermal growth factor (EGF); platelet-derived growth factor (PDGF); fibroblast growth factors (FGFs) such as FGF-5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; bone morphogenetic proteins (BMPs); interferons such as interferon-alpha, -beta, and -gamma; colony stimulating factors (CSFs), e.g., M-CSF, GM-CSF, and G-CSF; most interleukins; tumor necrosis factor (TNF) beta; follicle stimulating hormone; calcitonin; luteinizing hormone; anti-clotting factors such as Protein C; atrial natriuretic factor; lung surfactant; plasminogen activators, such as urokinase or human urine or tissue-type plasminogen activator (t-PA); hematopoietic growth factor; and enkephalinase. One of ordinary skill in the art will be aware of other growth factors or signaling molecules that can be expressed in accordance with the present invention.

Specific alterations in the glycosylation pattern of growth factors or other signaling molecules have been shown to have dramatic effects on their therapeutic properties. As but one non-limiting example, a common method of treatment for patients who suffer from chronic anemia is to provide them with frequent injections of recombinant human erythropoietin (rHuEPO) in order to boost their production of red blood cells. An analog of rHuEPO, darbepoetin alfa (Aranesp®), has been developed to have a longer duration in the body than normal rHuEPO. The primary difference between darbepoetin alfa and rHuEPO is the presence of two extra sialic-acid-containing N-linked oligosaccharide chains. Production of darbepoetin alfa has been accomplished using in vitro glycoengineering (see Elliott et al., Nature Biotechnology 21(4): 414-21, 2003). Elliott et al. used in vitro mutagenesis to incorporate extra glycosylation sites into the rHuEPO polypeptide backbone, resulting in expression of the darbepoetin alfa analog. The extra oligosaccharide chains are located distal to the EPO receptor binding site and apparently do not interfere with receptor binding. However, darbepoetin alfa's half-life is up to three-fold higher than rHuEPO, resulting in a much more effective therapeutic agent.

This example demonstrates that alterations in a growth factor or other signaling molecule's glycosylation pattern may have dramatic effects on the in vivo stability and/or activity of a therapeutic glycoprotein. Thus, expression of a growth factor or other signaling molecule of interest in accordance with the teachings of the present invention may result in the expressed growth factor or signaling molecule having an improved glycosylation pattern and improved therapeutic properties.

Receptors

Another class of glycoproteins that have been shown to be effective as pharmaceutical and/or commercial agents is receptors. Thus, production of receptors with desirable glycosylation patterns in accordance with the present invention is also of particular interest. Receptors are typically transmembrane glycoproteins that function by recognizing an extra-cellular signaling ligand. In addition to the ligand recognizing domain, receptors often have a protein kinase domain that initiates a signaling pathway by phosphorylating target intracellular molecules upon binding the ligand, leading to developmental or metabolic changes within the cell.

In certain embodiments, the glycoprotein receptor to be produced in accordance with the present invention is a receptor tyrosine kinase (RTK). The RTK family includes receptors that are crucial for a variety of functions numerous cell types (see, e.g., Yarden and Ullrich, *Ann. Rev. Biochem.* 57:433-478, 1988; Ullrich and Schlessinger, *Cell* 61:243-254, 1990, incorporated herein by reference). Non-limiting examples of RTKs include members of the fibroblast growth factor (FGF) receptor family, members of the epidermal growth factor (EGF) receptor family, platelet derived growth factor (PDGF) receptor, tyrosine kinase with immunoglobulin and EGF homology domains-1 (TIE-1) and TIE-2 receptors (Sato et al., *Nature* 376(6535):70-74, 1995) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., Oncogene 6:1677-83, 1991) or vascular endothelial cell growth factor receptor 2 (VEGFR-2)), fms-like tyrosine kinase-1 (Flt-1) (DeVries et al. Science 255; 989-991, 1992; Shibuya et al., Oncogene 5:519-524, 1990), sometimes referred to as vascular endothelial cell growth factor receptor 1 (VEGFR-1), neuropilin-1, endoglin, endosialin, and Axl. In certain embodiments, tumor necrosis factor alpha and beta receptors (TNFR-1; EP 417,563 published Mar. 20, 1991; and TNFR-2, EP 417,014 published Mar. 20, 1991) are expressed in accordance with the present invention (for review, see Naismith and Sprang, *J. Inflamm.* 47(1-2):1-7, 1995-96, incorporated herein by reference).

In certain embodiments, a glycoprotein receptor to be produced in accordance with the present invention is a G-protein coupled receptor (GPCR). GPCRs are glycoproteins that have seven transmembrane domains. Upon binding of a ligand to a GPCR, a signal is transduced within the cell which results in a change in a biological or physiological property of the cell. GPCRs are a major target for drug action and development. In fact, receptors have led to more than half of the currently known drugs (Drews, Nature Biotechnology, 14:1516, 1996) and GPCRs represent the most important target for therapeutic intervention with 30% of clinically prescribed drugs either antagonizing or agonizing a GPCR (Milligan, G. and Rees, S., TIPS, 20: 118-124, 1999). Since such receptors have an established, proven history as therapeutic targets, production of GPCRs with desirable glycosylation patterns in accordance with the present invention is also of particular interest. For example, extracellular domains of GPCRs with desirable glycosylation patterns expressed in accordance with the teachings of the present invention might function as important therapeutic agents by titrating or sequestering a ligand whose binding to an endogenous GPCR is detrimental.

GPCRs, along with G-proteins and effectors (intracellular enzymes and channels which are modulated by G-proteins), are the components of a modular signaling system that connects the state of intracellular second messengers to extracellular inputs. Such genes and gene-products are potential causative agents of disease.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of *D. discoideum*; and Family V, the fungal mating pheromone receptors such as STE2.

GPCRs include receptors for biogenic amines, for lipid mediators of inflammation, peptide hormones, and sensory signal mediators. The GPCR becomes activated when the receptor binds its extracellular ligand. Conformational changes in the GPCR, which result from the ligand-receptor interaction, affect the binding affinity of a G protein to the GPCR intracellular domains. This enables GTP to bind with enhanced affinity to the G protein.

Activation of the G protein by GTP leads to the interaction of the G protein α subunit with adenylate cyclase or other second messenger molecule generators. This interaction regulates the activity of adenylate cyclase and hence production of a second messenger molecule, cAMP. cAMP regulates phosphorylation and activation of other intracellular proteins. Alternatively, cellular levels of other second messenger molecules, such as cGMP or eicosinoids, may be upregulated or downregulated by the activity of GPCRs. The G protein α subunit is deactivated by hydrolysis of the GTP by GTPase, and the α, Βeτα, and γ subunits reassociate. The heterotrimeric G protein then dissociates from the adenylate cyclase or other second messenger molecule generator. Activity of GPCR may also be regulated by phosphorylation of the intra- and extracellular domains or loops.

Glutamate receptors form a group of GPCRs that are important in neurotransmission. Glutamate is the major neurotransmitter in the CNS and is believed to have important roles in neuronal plasticity, cognition, memory, learning and some neurological disorders such as epilepsy, stroke, and neurodegeneration (Watson, S, and S. Arkinstall, 1994) The G-Protein Linked Receptor Facts Book, Academic Press, San Diego Calif., pp. 130-132). These effects of glutamate are mediated by two distinct classes of receptors termed ionotropic and metabotropic. Ionotropic receptors contain an intrinsic cation channel and mediate fast excitatory actions of glutamate. Metabotropic receptors are modulatory, increasing the membrane excitability of neurons by inhibiting calcium dependent potassium conductances and both inhibiting and potentiating excitatory transmission of ionotropic receptors. Metabotropic receptors are classified into five subtypes based on agonist pharmacology and signal transduction pathways and are widely distributed in brain tissues. N-linked glycosylation has been shown to be important in the function of the human type 1 alpha metabotropic glutamate (mGlu1alpha) receptor (Mody et al., Neuropharmacology 38(10):1485-92, 1999). mGlu1alpha is normally expressed, at least in part, as a dimer consisting of monomers of approx. 145 and 160 KDa. By treating mGlu1alpha with tunicamycin, a potent inhibitor of N-linked glycosylation, Mody et al. demonstrated that although cell surface expression was not affected, only a single peptide with a mass of 130 kDa predicted by its primary amino acid sequence was expressed. Functionally, treatment with tunicamycin reduced agonist-stimulated phosphoinositide hydrolysis by approximately 50% compared to non-treated cell populations. Thus, adjusting the glycosylation patterns of GPCRs expressed according to the present inventive system may be useful in modulating the signaling function of the expressed GPCR and potentially to control or affect the pharmaceutical or other properties of the expressed GPCR.

The vasoactive intestinal polypeptide (VIP) family is a group of related polypeptides whose actions are also mediated by GPCRs. Key members of this family are VIP itself, secretin, and growth hormone releasing factor (GRF). VIP has a wide profile of physiological actions including relaxation of smooth muscles, stimulation or inhibition of secretion in various tissues, modulation of various immune cell activities, and various excitatory and inhibitory activities in the CNS. Secretin stimulates secretion of enzymes and ions in the pancreas and intestine and is also present in small amounts in the brain. Glycosylation of the VIP receptor has been shown to have an important effect on the binding of its cognate VIP (Chochola et al., J. Biol. Chem. 268: 2312-2318, 1993). Sterically blocking the oligosaccharide chains by treating the VIP receptor with wheat germ agglutinin markedly inhibited VIP binding in a dose dependent manner and reduced the VIP-stimulated cAMP response. Additionally, mutation of specific N-linked glycosylation sites in the VIP receptor resulted in retention of the receptor in the endoplasmic reticulum, indicating that proper glycosylation was critical for delivery to the cell surface (Couvineau et al., Biochemistry 35(6):1745-52, 1996). Thus, adjusting the glycosylation patterns of GPCRs expressed according to the present inventive system may be useful in modulating (for example, either increasing or decreasing) binding of the expressed GPCR to its cognate ligand and potentially to control or affect the pharmaceutical or other properties of the expressed GPCR.

In general, practitioners of the present invention will select a glycoprotein of interest, and will know its precise amino acid sequence. The techniques of the present invention have been successfully applied to both O-linked (Examples 2 and 3) and N-linked (Examples 4 and 5) glycoproteins, indicating that the present invention will be useful for the expression of glycoproteins generally. Any given glycoprotein that is to be expressed in accordance with the present invention may have its own particular characteristics and may influence the cell density or viability of the cultured cells, may be expressed at lower levels than another glycoprotein grown under identical culture conditions, and may be differently glycosylated at one or more sites depending on the exact culture conditions and steps performed. One of ordinary skill in the art will be able to appropriately modify the steps and compositions used to produce a particular glycoprotein according to the teachings of the present invention in order to optimize cell growth and the production and/or the glycosylation pattern of any given expressed glycoprotein.

In certain embodiments, tumor necrosis factor inhibitors, in the form of tumor necrosis factor alpha and beta receptors (TNFR-1; EP 417,563 published Mar. 20, 1991; and TNFR-2, EP 417,014 published Mar. 20, 1991, each of which is incorporated herein by reference in its entirety) are expressed in accordance with systems and methods of the present invention (for review, see Naismith and Sprang, J. Inflamm. 47(1-2):1-7, 1995-96, incorporated herein by reference in its entirety). According to some embodiments, a tumor necrosis factor inhibitor comprises a soluble TNF receptor. In certain embodiments, a tumor necrosis factor inhibitor comprises a soluble TNFR-Ig. In certain embodiments, TNF inhibitors of the present invention are soluble forms of TNFRI and TNFRII. In certain embodiments, TNF inhibitors of the present invention are soluble TNF binding proteins. In certain embodiments, TNF inhibitors of the present invention are TNFR-Ig fusion proteins, e.g., TNFR-Fc or etanercept. As used herein, "etanercept," refers to TNFR-Fc, which is a dimer of two molecules of the extracellular portion of the p75 TNF-α receptor, each molecule consisting of a 235 amino acid Fc portion of human IgG1.

Introduction of Genes for the Expression of Glycoproteins into Host Cells

Generally, a nucleic acid molecule introduced into the cell encodes the glycoprotein desired to be expressed according to the present invention. Alternatively, a nucleic acid molecule may encode a gene product that induces the expression of the desired glycoprotein by the cell. For example, introduced genetic material may encode a transcription factor that activates transcription of an endogenous or heterologous glycoprotein. Alternatively or additionally, an introduced nucleic acid molecule may increase the translation or stability of a glycoprotein expressed by the cell.

Methods suitable for introducing nucleic acids sufficient to achieve expression of a glycoprotein of interest into mammalian host cells are known in the art. See, for example, Gething et al., Nature, 293:620-625, 1981; Mantei et al., Nature, 281: 40-46, 1979; Levinson et al. EP 117,060; and EP 117,058, each of which is incorporated herein by reference. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in U.S. Pat. No. 4,399,216 issued Aug. 16, 1983. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988.

In some embodiments, a nucleic acid to be introduced is in the form of a naked nucleic acid molecule. For example, the nucleic acid molecule introduced into a cell may consist only of the nucleic acid encoding the glycoprotein and the necessary genetic control elements. Alternatively, a nucleic acid encoding the glycoprotein (including the necessary regulatory elements) may be contained within a plasmid vector. Non-limiting representative examples of suitable vectors for expression of glycoproteins in mammalian cells include pcDNA1; pCD, see Okayama, et al. Mol. Cell. Biol. 5:1136-1142, 1985; pMClneo Poly-A, see Thomas, et al. Cell 51:503-512, 1987; abaculovirus vector such as pAC 373 or pAC 610; CDM8, see Seed, B. Nature 329:840, 1987; and pMT2PC, see Kaufman, et al. EMBO J. 6:187-195, 1987, each of which is incorporated herein by reference in its entirety. In some embodiments, a nucleic acid molecule to be introduced into a cell is contained within a viral vector. For example, a nucleic acid encoding the glycoprotein may be inserted into the viral genome (or a partial viral genome). Regulatory elements directing the expression of the glycoprotein may be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (e.g., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection.

Alternatively, naked DNA can also be introduced into cells by complexing the DNA to a cation, such as polylysine, which is coupled to a ligand for a cell-surface receptor (see for example Wu, G. and Wu, C. H. J. Biol. Chem. 263:14621, 1988; Wilson et al. J. Biol. Chem. 267:963-967, 1992; and U.S. Pat. No. 5,166,320, each of which is hereby incorporated by reference in its entirety). Binding of the DNA-ligand complex to the receptor facilitates uptake of the DNA by receptor-mediated endocytosis.

Use of viral vectors containing particular nucleic acid sequences, e.g., a cDNA encoding a glycoprotein, is a common approach for introducing nucleic acid sequences into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are generally expressed efficiently in cells that have taken up viral vector nucleic acid.

Defective retroviruses are well characterized for use in gene transfer for gene therapy purposes (for a review see Miller, A. D. Blood 76:271, 1990). A recombinant retrovirus can be constructed having a nucleic acid encoding a glycoprotein of interest inserted into the retroviral genome. Additionally, portions of the retroviral genome can be removed to render the retrovirus replication defective. Such a replication defective retrovirus is then packaged into virions which can be used to infect a target cell through the use of a helper virus by standard techniques.

The genome of an adenovirus can be manipulated such that it encodes and expresses a glycoprotein of interest but is inactivated in terms of its ability to replicate in a normal lytic viral life cycle. See, for example, Berkner et al. BioTechniques 6:616, 1988; Rosenfeld et al. Science 252:431-434, 1991; and Rosenfeld et al. Cell 68:143-155, 1992. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses are advantageous in that they do not require dividing cells to be effective gene delivery vehicles and can be used to infect a wide variety of cell types, including airway epithelium (Rosenfeld et al., 1992, cited supra), endothelial cells (Lemarchand et al., Proc. Natl. Acad. Sci. USA 89:6482-6486, 1992), hepatocytes (Herz and Gerard, Proc. Natl. Acad. Sci. USA 90:2812-2816, 1993) and muscle cells (Quantin et al., Proc. Natl. Acad. Sci. USA 89:2581-2584, 1992). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, J. Virol. 57:267, 1986). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol., 158:97-129, 1992). It is also one of the few viruses that may integrate its DNA into non-dividing cells, and exhibits a high frequency of stable integration (see for example Flotte et al., Am. J. Respir. Cell. Mol. Biol. 7:349-356, 1992; Samulski et al., J. Virol. 63:3822-3828, 1989; and McLaughlin et al., J. Virol. 62:1963-1973, 1989). Vectors containing as little as 300 base pairs of AAV can be packaged and can integrate. Space for exogenous DNA is limited to about 4.5 kb. An AAV vector such as that described in Tratschin et al. (Mol. Cell. Biol. 5:3251-3260, 1985) can be used to introduce DNA into cells. A variety of nucleic acids have been introduced into different cell types using AAV vectors (see for example Hermonat et al., Proc. Natl. Acad. Sci. USA 81:6466-6470, 1984; Tratschin et al., Mol. Cell. Biol. 4:2072-2081, 1985; Wondisford et al., Mol. Endocrinol. 2:32-39, 1988; Tratschin et al., J. Virol. 51:611-619, 1984; and Flotte et al., J. Biol. Chem. 268:3781-3790, 1993).

When the method used to introduce nucleic acid molecules into a population of cells results in modification of a large proportion of the cells and efficient expression of the glycoprotein by the cells, the modified population of cells may be used without further isolation or subcloning of individual cells within the population. That is, there may be sufficient production of the glycoprotein by the population of cells such that no further cell isolation is needed and the population can be immediately be used to seed a cell culture for the production of the glycoprotein. Alternatively, it may be desirable to isolate and expand a homogenous population of cells from a few cells or a single cell that efficiently produce(s) the glycoprotein.

Alternative to introducing a nucleic acid molecule into a cell that encodes a glycoprotein of interest, the introduced nucleic acid may encode another polypeptide or protein that induces or increases the level of expression of the glycoprotein produced endogenously by a cell. For example, a cell may be capable of expressing a particular glycoprotein but may fail to do so without additional treatment of the cell. Similarly, the cell may express insufficient amounts of the glycoprotein for the desired purpose. Thus, an agent that stimulates expression of the glycoprotein of interest can be used to induce or increase expression of that glycoprotein by the cell. For example, the introduced nucleic acid molecule may encode a transcription factor that activates or upregulates transcription of the glycoprotein of interest. Expression of such a transcription factor in turn leads to expression, or more robust expression of the glycoprotein of interest.

In certain embodiments, a nucleic acid that directs expression of the glycoprotein is stably introduced into the host cell. In certain embodiments, a nucleic acid that directs expression of the glycoprotein is transiently introduced into the host cell. One of ordinary skill in the art will be able to choose whether to stably or transiently introduce a nucleic acid into the cell based on his or her experimental needs.

A gene encoding a glycoprotein of interest may optionally be linked to one or more regulatory genetic control elements. In certain embodiments, a genetic control element directs constitutive expression of the glycoprotein. In certain embodiments, a genetic control element that provides inducible expression of a gene encoding the glycoprotein of interest can be used. The use of an inducible genetic control element (e.g., an inducible promoter) allows for modulation of the production of the glycoprotein in the cell. Non-limiting examples of potentially useful inducible genetic control elements for use in eukaryotic cells include hormone-regulated elements (e.g., see Mader, S, and White, J. H., Proc. Natl. Acad. Sci. USA 90:5603-5607, 1993), synthetic ligand-regulated elements (see, e.g. Spencer, D. M. et al., Science 262: 1019-1024, 1993) and ionizing radiation-regulated elements (e.g., see Manome, Y. et al., Biochemistry 32:10607-10613, 1993; Datta, R. et al., Proc. Natl. Acad. Sci. USA 89:10149-10153, 1992). Additional cell-specific or other regulatory systems known in the art may be used in accordance with the invention.

One of ordinary skill in the art will be able to choose and, optionally, to appropriately modify the method of introducing genes that cause the cell to express the glycoprotein of interest in accordance with the teachings of the present invention.

Cells

Any host cell susceptible to cell culture, and to expression of glycoproteins, may be utilized in accordance with the present invention. In certain embodiments, a host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Additionally, any number of commercially and non-commercially available hybridoma cell lines that express glycoproteins may be utilized in accordance with the present invention. One skilled in the art will appreciate that hybridoma cell lines might have different nutrition requirements and/or might require different culture conditions for optimal growth and glycoprotein expression, and will be able to modify conditions as needed.

As noted above, in many instances the cells will be selected or engineered to produce high levels of glycoprotein. Often, cells will be manipulated by the hand of man to produce high levels of glycoprotein, for example by introduction of a gene encoding the glycoprotein of interest and/or by introduction of genetic control elements that regulate expression of that gene (whether endogenous or introduced).

One of ordinary skill in the art will appreciate that glycoproteins produced in different cell types may contain different resulting glycosylation patterns. For example, Przybylo et al. demonstrated that the glycosylation patterns of cadherins differed when expressed in non-malignant epithelial ureter cells, v-raf transfected HCV29 cells and transitional cell cancers of the urinary bladder (see Przybylo et al., Cancer Cell International, 2(1):6, 2002). Lifely et al. demonstrated that the glycosylation pattern and biological activity of a humanized IgG antibody differed when expressed in CHO, Y0 myeloma and NSO myeloma cell lines (see Lifely et al., Glycobiology. 5(8):813-22, 1995). One of ordinary skill in the art will be able to select a desirable cell line for production of a particular glycoprotein without undue experimentation. Regardless of which cell line is ultimately selected, a glycoprotein may be expressed in accordance with the present invention, resulting in a more extensive glycosylation pattern.

Certain glycoproteins may have detrimental effects on cell growth, cell viability or some other characteristic of the cells that ultimately limits production of the glycoprotein of interest in some way. Even amongst a population of cells of one particular type engineered to express a specific glycoprotein, variability within the cellular population exists such that certain individual cells will grow better, produce more glycoprotein of interest, produce a glycoprotein with a more extensive glycosylation pattern, or produce a glycoprotein whose glycosylation pattern more accurately reflects the glycosylation pattern of the naturally occurring glycoprotein. In certain embodiments, a cell line is empirically selected by the practitioner for robust growth under the particular conditions chosen for culturing the cells. In some embodiments, individual cells engineered to express a particular glycoprotein are chosen for large-scale production based on cell growth, final cell density, percent cell viability, titer of the expressed glycoprotein, extent and composition of the oligosaccharide side chains or any combination of these or any other conditions deemed important by the practitioner.

Culturing the Cells

The present invention may be used with any cell culture method that is amenable to the expression of glycoproteins. For example, cells may be grown in batch or fed-batch cultures, where the culture is terminated after sufficient expression of the glycoprotein, after which the expressed glycoprotein is harvested. Alternatively, cells may be grown in perfusion cultures, where the culture is not terminated and new nutrients and other components are periodically or continuously added to the culture, during which the expressed glycoprotein is harvested periodically or continuously.

Cells may be grown in any convenient volume chosen by the practitioner. For example, cells may be grown in small scale reaction vessels ranging in volume from a few milliliters to several liters. Alternatively, cells may be grown in large scale commercial Bioreactors ranging in volume from approximately at least 1 liter to 10, 100, 250, 500, 1000, 2500, 5000, 8000, 10,000, 12,000 liters or more, or any volume in between The temperature of a cell culture will be selected based primarily on the range of temperatures at which the cell culture remains viable, the range in which a high level of glycoprotein is produced and/or the range in which the expressed glycoprotein contains a desirable glycosylation pattern. For example, CHO cells grow well and can produce glycoproteins with desirable glycosylation patterns at commercially adequate levels at approximately 37° C. In general, most mammalian cells grow well and can produce glycoproteins with desirable glycosylation patterns at commercially adequate levels within a range of about 25° C. to 42° C., although methods taught by the present disclosure are not limited to these temperatures. Certain mammalian cells grow well and can produce glycoproteins with desirable glycosylation patterns at commercially adequate levels within the range of about 35° C. to 40° C. In certain embodiments, a cell culture is grown at a temperature of 20, 21, 22, 23, 24, 25, 26, 27, 28, 29, 30, 31, 32, 33, 34, 35, 36, 37, 38, 39, 40, 41, 42, 43, 44, 45° C. at one or more times during the cell culture process.

Those of ordinary skill in the art will be able to select appropriate temperature or temperatures in which to grow cells, depending on the particular needs of the cells and the particular production requirements of the practitioner.

Furthermore, a culture may be subjected to one or more temperature shifts during the course of the culture. When shifting the temperature of a culture, the temperature shift may be relatively gradual. For example, it may take several hours or days to complete the temperature change. Alternatively, the temperature shift may be relatively abrupt. The temperature may be steadily increased or decreased during the culture process. Alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple discrete temperature shifts are encompassed in this embodiment. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

As with the initial temperature or temperature range, the temperature or temperature range of a cell culture after the temperature shift(s) is generally selected based primarily on the temperature(s) at which the cell culture remains viable, the range in which a high level of glycoprotein is produced and/or the range in which the expressed glycoprotein contains a desirable glycosylation pattern. In general, most mammalian cells remain viable and express glycoproteins with desirable glycosylation patterns at commercially adequate levels within a range of about 25° C. to 42° C., although methods taught by the present disclosure are not limited to these temperatures. In certain embodiments, mammalian cells remain viable and express glycoproteins with desirable glycosylation patterns at commercially adequate levels within a range of about 25° C. to 35° C. Those of ordinary skill in the art will be able to select appropriate temperature(s) or temperature range(s) in which to grow cells, depending on the particular needs of the cells and the particular production requirements of the practitioner. The cells may be grown for any amount of time, depending on the needs of the practitioner and the requirement of the cells themselves.

In certain embodiments, batch and fed-batch reactions are terminated once the expressed glycoprotein reaches a sufficiently high titer and/or once the expressed glycoprotein exhibits a desirable glycosylation pattern, as determined by the needs of the practitioner. Additionally or alternatively, batch and fed-batch reactions may be terminated once the cells reach a sufficiently high density, as determined by the needs of the practitioner. For example, the culture may be terminated once the cells reach 1, 5, 10, 15, 20, 25, 30, 35, 40, 45, 50, 55, 60, 65, 70, 75, 80, 85, 90, 95 or 99 percent of maximal viable cell density. Additionally or alternatively, batch and fed-batch reactions may be terminated prior to excessive accumulation of metabolic waste products such as lactate and ammonium.

In certain cases, it may be beneficial to supplement a cell culture during the subsequent production phase with nutrients or other medium components that have been depleted or metabolized by the cells. As non-limiting examples, it may be beneficial to supplement a cell culture with hormones and/or other growth factors, inorganic ions (such as, for example, sodium, chloride, calcium, magnesium, and phosphate), buffers, vitamins, nucleosides or nucleotides, trace elements (inorganic compounds usually present at very low final concentrations), amino acids, lipids, or glucose or other energy source. Such supplementary components may all be added to the cell culture at one time, or they may be provided to the cell culture in a series of additions.

In certain embodiments, cells are grown in accordance with any of the cell culture methods described in U.S. Provisional Patent Application Ser. No. 60/605,097, incorporated herein by reference. In certain embodiments, cells are grown under one or more of the conditions described in U.S. patent application Ser. No. 11/213,308, incorporated herein by reference.

One of ordinary skill in the art will be able to tailor specific cell culture conditions in order to optimize certain characteristics of the cell culture including but not limited to growth rate, cell viability, final cell density of the cell culture, final concentration of detrimental metabolic byproducts such as lactate and ammonium, final titer of the expressed glycoprotein, extent and composition of the oligosaccharide side chains or any combination of these or other conditions deemed important by the practitioner.

Isolation of the Expressed Glycoprotein

In general, it will typically be desirable to isolate and/or purify glycoproteins expressed according to the present invention. In certain embodiments, the expressed glycoprotein is secreted into the medium and thus cells and other solids may be removed, as by centrifugation or filtering for example, as a first step in the purification process.

Alternatively, the expressed glycoprotein may be bound to the surface of the host cell. For example, the media may be removed and the host cells expressing the glycoprotein are lysed as a first step in the purification process. Lysis of mammalian host cells can be achieved by any number of means well known to those of ordinary skill in the art, including physical disruption by glass beads and exposure to high pH conditions.

The expressed glycoprotein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, *Protein Purification Principles and Practice* 2nd Edition, Springer-Verlag, New York, 1987; Higgins, S. J. and Hames, B. D. (eds.), *Protein Expression: A Practical Approach*, Oxford Univ Press, 1999; and Deutscher, M. P., Simon, M. I., Abelson, J. N. (eds.), *Guide to Protein Purification: Methods in Enzymology* (Methods in Enzymology Series, Vol. 182), Academic Press, 1997, each of which is incorporated herein by reference). For immunoaffinity chromatography in particular, the glycoprotein may be isolated by binding it to an affinity column comprising antibodies that were raised against that glycoprotein and were affixed to a stationary support. Alternatively, affinity tags such as an influenza coat sequence, poly-histidine, or glutathione-S-transferase can be attached to the glycoprotein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the glycoprotein during the purification process. Protease inhibitors are particularly advantageous when cells must be lysed in order to isolate and purify the expressed glycoprotein. Additionally or alternatively, glycosidase inhibitors may be added at any or all stages in order to reduce or eliminate enzymatic trimming of the covalently attached oligosaccharide chains.

Glycoproteins expressed according to the present invention may have more extensive, or otherwise altered, glycosylation patterns than they would if grown under traditional cell culture conditions. Thus, one practical benefit of the present invention that may be exploited at the purification step is that the additional and/or altered sugar residues on a glycoprotein grown in accordance with certain of the present inventive methods may confer on it distinct biochemical properties that may be used by the practitioner to purify that glycoprotein more easily, or to a greater purity, than would be possible for a glycoprotein grown in accordance with more traditional methods.

One of ordinary skill in the art will appreciate that the exact purification technique will vary depending on the character of the glycoprotein to be purified, the character of the cells from which the glycoprotein is expressed, and/or the composition of the medium in which the cells were grown.

Immunogenic Compositions

Glycoproteins produced according to the teachings of the present disclosure may also be used in immunogenic compositions, e.g., as vaccines. In certain embodiments, an improved glycosylation pattern achieved by producing glycoproteins in accordance with certain methods of the present invention may result in a more effective immunogenic composition. For example, the immunogenic composition containing the produced glycoprotein may trigger a more effective immune response in which the subject's immune system produces a greater number of antibodies to the glycoprotein and/or produces antibodies that exhibit a greater specificity for a the immunogenic glycoprotein. Additionally or alternatively, such a glycoprotein may trigger an immune response with fewer and/or less severe side effects. In certain embodiments, immunogenic compositions of the invention comprise one or more glycoproteins. Additionally or alternatively, an inventive immunogenic composition may include one or more physiologically acceptable carriers.

In general, selection of the appropriate "effective amount" or dosage for components of an inventive immunogenic composition(s) is based upon a variety of factors, including but not limited to, the identity of the selected glycoprotein(s) in the immunogenic composition employed, the glycosylation pattern of the glycoprotein(s), and the physical condition of the subject, most especially including the general health, age and/or weight of the immunized subject. As is known in the art, the particular methods and routes of administration and the presence of additional components in the immunogenic compositions may also affect the dosages and amounts of the DNA plasmid compositions. Such selection and upward or downward adjustment of the effective dose is within the skill of the art. The amount of immunogenic composition required to induce an immune response, including but not limited to a protective response, or produce an exogenous effect in the patient without significant adverse side effects varies depending upon these factors. Suitable doses are readily determined by persons skilled in the art.

Certain immunogenic compositions of the present invention may contain an adjuvant. An adjuvant is a substance that enhances the immune response when administered together with an immunogen or antigen. A number of cytokines or lymphokines have been shown to have immune modulating activity, and thus may be used as adjuvants, including, but not limited to, the interleukins 1-$\alpha$, 1-$\beta$, 2, 4, 5, 6, 7, 8, 10, 12 (see, e.g., U.S. Pat. No. 5,723,127, incorporated herein by reference in its entirety), 13, 14, 15, 16, 17 and 18 (and its mutant forms), the interferons-$\alpha$, $\beta$ and $\gamma$, granulocyte-macrophage colony stimulating factor (see, e.g., U.S. Pat. No. 5,078,996, incorporated herein by reference in its entirety), macrophage colony stimulating factor, granulocyte colony stimulating factor, GSF, and the tumor necrosis factors $\alpha$ and $\beta$. Still other adjuvants useful in this invention include a chemokine, including without limitation, MCP-1, MIP-1$\alpha$, MIP-10, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, K1LLER, TRAIL-R2, TRICK2, and DR6. Still another adjuvant molecule includes Caspase (ICE). See, also International Patent Publication Nos. WO98/17799 and WO99/43839, each of which is incorporated herein by reference in its entirety.

Also useful as adjuvants are cholera toxins (CT) and mutants thereof, including those described in published International Patent Application number WO 00/18434 (wherein the glutamic acid at amino acid position 29 is replaced by another amino acid (other than aspartic acid), preferably a histidine). Similar CTs or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36). Each of these references is incorporated herein in its entirety.

In certain embodiments, immunogenic compositions of the present invention are administered to a human or to a non-human vertebrate by a variety of routes including, but not limited to, intranasal, oral, vaginal, rectal, parenteral, intradermal, transdermal (see for example, International patent publication No. WO 98/20734, which is hereby incorporated by reference in its entirety), intramuscular, intraperitoneal, subcutaneous, intravenous and intraarterial. The appropriate route may be selected depending on the nature of the immunogenic composition used, an evaluation of the age, weight, sex and general health of the patient and the antigens present in the immunogenic composition, and/or other factors known to those of ordinary skill in the art.

In certain embodiments, immunogenic compositions are administered at multiple times. The order of immunogenic composition administration and the time periods between individual administrations may be selected by one of skill in the art based upon relevant factors known to those of ordinary skill in the art, including, but not limited to, the physical characteristics and precise responses of the host to the application of the method.

Pharmaceutical Formulations

In certain embodiments, produced glycoproteins will have pharmacologic activity and will be useful in the preparation of pharmaceuticals. Inventive compositions as described above may be administered to a subject or may first be formulated for delivery by any available route including, but not limited to parenteral (e.g., intravenous), intradermal, subcutaneous, oral, nasal, bronchial, opthalmic, transdermal (topical), transmucosal, rectal, and vaginal routes. Inventive pharmaceutical compositions typically include a purified glycoprotein expressed from a mammalian cell line, a delivery agent (i.e., a cationic polymer, peptide molecular transporter, surfactant, etc., as described above) in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. For example, a glycoprotein produced according to the present invention may be additionally conjugated to other drugs for systemic pharmacotherapy, such as toxins, low-molecular-weight cytotoxic drugs, biological response modifiers, and radionuclides (see e.g., Kunz et al., *Calicheamicin derivative-carrier conjugates*, US20040082764 A1).

Alternatively or additionally, a protein or polypeptide produced according to the present invention may be administered in combination with (whether simultaneously or sequentially) one or more additional pharmaceutically active agents. An exemplary list of these pharmaceutically active agents can be found in the Physicians' Desk Reference, 55 Edition, published by Medical Economics Co., Inc., Montvale, N.J., 2001, incorporated herein by reference. For many of these listed agents, pharmaceutically effective dosages and regimens are known in the art; many are presented in the Physicians' Desk Reference itself.

A pharmaceutical composition is advantageously formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Certain pharmaceutical formulations of the present invention are stable under the conditions of manufacture and storage and must be preserved against the contaminating action of microorganisms such as bacteria and fungi. In general, a relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be advantageous to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified glycoprotein in the required amount in an appropriate solvent with one or a combination of ingredients enumerated above, as required, followed by filtered sterilization. Generally, dispersions are prepared by incorporating the purified glycoprotein expressed from a mammalian cell line into a sterile vehicle which contains a basic dispersion medium and the required other ingredients from those enumerated above. In the case of sterile powders for the preparation of sterile injectable solutions, methods of preparation include, for example, vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified glycoprotein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions comprising a purified glycoprotein expressed from a mammalian cell line and a delivery agent are advantageously delivered in the form of an aerosol spray from a pressured container or dispenser which contains a suitable propellant, e.g., a gas such as carbon dioxide, or a nebulizer. The present invention particularly contemplates delivery of the compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and the delivery agents of the invention will enhance cellular uptake. According to certain embodiments, compositions comprising a purified glycoprotein expressed from a mammalian cell line and a delivery agent are formulated as large porous particles for aerosol administration.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified glycoprotein and delivery agents are formulated into ointments, salves, gels, or creams as generally known in the art.

Compositions can also be prepared in the form of suppositories (e.g., with conventional suppository bases such as cocoa butter and other glycerides) or retention enemas for rectal delivery.

In certain embodiments, inventive pharmaceutical compositions contain optional excipients such as a local anesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Such facilitating agents include the local anesthetics bupivacaine or tetracaine (see for example, U.S. Pat. Nos. 5,593,972; 5,817,637; 5,380,876; 5,981,505 and 6,383,512 and International Patent Publication No. WO98/17799, each of which is hereby incorporated by reference in its entirety).

In certain embodiments, compositions are prepared with carriers that will protect the glycoprotein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. Such suspensions can be prepared according to methods known to those skilled in the art, for example, as described in U.S. Pat. No. 4,522,811, incorporated herein by reference in its entirety.

It may be advantageous to formulate oral or parenteral compositions in unit dosage form for ease of administration and uniformity of dosage. Unit dosage form as used herein refers to physically discrete units suited as unitary dosages for the subject to be treated, each unit containing a predetermined quantity of active glycoprotein calculated to produce the desired therapeutic effect in association with the required pharmaceutical carrier.

A glycoprotein expressed according to the present invention can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with a glycoprotein as described herein can include a single treatment or, in many cases, can include a series of treatments. It will be understood that appropriate doses may depend upon the potency of the glycoprotein and may optionally be tailored to the particular recipient, for example, through administration of increasing doses until a preselected desired response is achieved. It will furthermore be understood that the specific dose level for any particular animal subject may depend upon a variety of factors including the activity of the specific glycoprotein employed, the age, body weight, general health, gender, and diet of the subject, the time of administration, the route of administration, the rate of excretion, any drug combination, and/or the degree of expression or activity to be modulated.

The present invention includes the use of inventive compositions for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, $8^{th}$ edition, Iowa State University Press; ISBN: 0813817439; 2001.

Inventive pharmaceutical compositions can be included in a container, pack, or dispenser together with instructions for administration.

The foregoing description is to be understood as being representative only and is not intended to be limiting. Alternative methods and materials for implementing the invention and also additional applications will be apparent to one of skill in the art, and are intended to be included within the accompanying claims.

EXAMPLES

Example 1

Media Formulations

The present invention encompasses the finding that glycoproteins produced by a culture of cells grown in culture media containing manganese at one or more inventive concentrations contain more extensive glycosylation patterns than they otherwise would if the cells were grown in traditional media. Manganese may be added to any culture medium that is capable of supporting cell growth. Exemplary culture media to which manganese may be added to within any of the inventive concentrations are listed in Table 1, although the present invention is not limited to the utilization of these culture media. As will be understood by one of ordinary skill in the art, other culture media may be utilized to grow cells and/or certain alterations may be made to the compositions of the exemplary culture media listed in Table 1.

TABLE 1

Exemplary culture media.

| Amino Acids | Medium A | | Medium B | | Medium C | | Medium D | | Medium E | |
|---|---|---|---|---|---|---|---|---|---|---|
| | mg/L | mM | mg/L | mM | mg/L | mM | mg/L | mM | mg/L | mM |
| alanine | 96.03 | 1.08 | 24.87 | 0.28 | 17.80 | 0.20 | | | 24.87 | 0.28 |
| arginine | 1186.99 | 6.82 | 423.43 | 2.43 | 347.97 | 2.00 | 84.00 | 0.40 | 423.43 | 2.43 |

TABLE 1-continued

Exemplary culture media.

|  | Medium A | | Medium B | | Medium C | | Medium D | | Medium E | |
| --- | --- | --- | --- | --- | --- | --- | --- | --- | --- | --- |
| asparagine•H₂O | 713.59 | 4.76 | 173.90 | 1.16 | 75.00 | 0.50 | | | 173.90 | 1.16 |
| aspartic acid | 318.53 | 2.39 | 52.72 | 0.40 | 26.20 | 0.20 | | | 52.72 | 0.40 |
| cysteine•HCl•H₂O | 70.01 | 0.40 | 70.01 | 0.40 | 70.19 | 0.40 | 35.10 | 0.20 | 70.01 | 0.40 |
| cysteine•2HCl | 297.09 | 0.95 | 62.09 | 0.20 | 62.25 | 0.20 | | | 62.09 | 0.20 |
| glutamic acid | | | | | 29.40 | 0.20 | | | | |
| monosodium glutamate | 158.59 | 1.08 | 41.08 | 0.28 | | | | | 41.08 | 0.28 |
| glutamine | 1892.40 | 12.96 | 1162.40 | 7.96 | 1163.95 | 7.97 | 584.60 | 4.00 | 1162 | 7.96 |
| glycine | 95.88 | 1.28 | 35.92 | 0.48 | 30.00 | 0.40 | 30.00 | 0.40 | 35.92 | 0.48 |
| histidine•HCl•H₂O | 369.10 | 1.76 | 75.27 | 0.36 | 46.00 | 0.22 | 42.00 | 0.20 | 75.27 | 0.36 |
| isoleucine | 623.63 | 4.76 | 151.90 | 1.16 | 104.99 | 0.80 | 104.80 | 0.80 | 151.90 | 1.16 |
| leucine | 852.31 | 6.51 | 172.69 | 1.32 | 104.99 | 0.80 | 104.80 | 0.80 | 172.69 | 1.32 |
| lysine•HCl | 945.96 | 5.20 | 218.38 | 1.20 | 145.99 | 0.80 | 146.20 | 0.80 | 218.38 | 1.20 |
| methionine | 291.82 | 1.96 | 53.55 | 0.36 | 29.80 | 0.20 | 30.00 | 0.20 | 53.55 | 0.36 |
| phenylalanine | 428.62 | 2.60 | 98.81 | 0.60 | 65.99 | 0.40 | 66.00 | 0.40 | 98.81 | 0.60 |
| proline | 372.25 | 3.24 | 96.40 | 0.84 | 68.99 | 0.60 | | | 96.40 | 0.84 |
| serine | 904.71 | 8.62 | 273.07 | 2.60 | 126.00 | 1.20 | | | 273.07 | 2.60 |
| threonine | 513.39 | 4.31 | 132.81 | 1.12 | 94.99 | 0.80 | 95.20 | 0.80 | 132.81 | 1.12 |
| tryptophan | 159.32 | 0.78 | 28.99 | 0.14 | 16.00 | 0.08 | 16.00 | 0.08 | 28.99 | 0.14 |
| tyrosine•2Na•2H₂O | 560.81 | 2.15 | 145.10 | 0.56 | 103.79 | 0.40 | 89.46 | 0.40 | 145.10 | 0.56 |
| valine | 505.36 | 4.32 | 131.17 | 1.12 | 93.99 | 0.80 | 93.60 | 0.80 | 131.17 | 1.12 |
| Vitamins | mg/L | μM | mg/L | μM | mg/L | μM | mg/L | μM | mg/L | μM |
| biotin | 2.00 | 8.21 | 0.36 | 1.49 | 0.20 | 0.821 | | | 0.36 | 1.49 |
| calcium pantothenate | 22.02 | 46.27 | 4.03 | 8.47 | 2.24 | 4.71 | 4.00 | 8.40 | 4.03 | 8.47 |
| choline chloride | 87.67 | 630.74 | 16.11 | 115.92 | 8.99 | 64.31 | 4.00 | 28.60 | 16.11 | 115.92 |
| folic acid | 25.95 | 58.84 | 4.76 | 10.80 | 2.65 | 6.01 | 4.00 | 9.10 | 4.76 | 10.80 |
| inositol | 123.39 | 685.47 | 22.64 | 125.79 | 12.60 | 70.00 | 7.00 | 38.90 | 22.64 | 125.79 |
| nicotinamide | 19.60 | 160.70 | 3.61 | 29.62 | 2.02 | 16.56 | 4.00 | 32.80 | 3.61 | 29.62 |
| pyridoxal•HCl | 1.99 | 9.83 | 1.99 | 9.83 | 2.00 | 9.89 | 4.00 | 19.60 | 1.99 | 9.83 |
| pyridoxine•HCl | 18.06 | 87.67 | 1.67 | 8.10 | 0.03 | 0.15 | | | 1.67 | 8.10 |
| riboflavin | 2.20 | 5.85 | 0.40 | 1.06 | 0.22 | 0.58 | 0.40 | 1.10 | 0.40 | 1.06 |
| thiamine•HCl | 21.51 | 63.84 | 3.92 | 11.64 | 2.17 | 6.44 | 4.00 | 11.90 | 3.92 | 11.64 |
| vitamin B12 | 6.93 | 5.12 | 1.34 | 0.99 | 0.78 | 0.58 | | | 1.34 | 0.99 |
| Inorganic Salts | mg/L | mM | mg/L | mM | mg/L | mM | mg/L | mM | mg/L | mM |
| CaCl₂ | 115.78 | 1.04 | 115.78 | 1.04 | 116.1 | 1.046 | 200.0 | 1.80 | 115.78 | 1.04 |
| KCl | 310.94 | 4.17 | 310.94 | 4.17 | 311.8 | 4.179 | 400.0 | 5.40 | 310.94 | 4.17 |
| Na₂HPO₄ | 70.81 | 0.50 | 70.81 | 0.50 | 71.0 | 0.500 | | | 70.81 | 0.50 |
| NaCl | 1104.96 | 18.92 | 3704.96 | 63.44 | 5539.0 | 94.846 | 6400.0 | 110.30 | 3704 | 63.44 |
| NaH₂PO₄•H₂O | 636.33 | 4.61 | 114.53 | 0.83 | 62.5 | 0.453 | 140.0 | 0.91 | 114.33 | 0.83 |
| MgSO₄ | 48.70 | 0.41 | 48.70 | 0.41 | 48.8 | 0.407 | | | 48.70 | 0.41 |
| MgSO₄•7H₂O | 95.00 | 0.39 | 8.60 | 0.03 | | | 200.0 | 0.80 | 8.60 | 0.03 |
| MgCl₂ | 28.53 | 0.30 | 28.53 | 0.30 | 28.6 | 0.301 | | | 28.53 | 0.30 |
| NaHCO₃ | 2000.00 | 23.81 | 1220.00 | 14.52 | 2440.0 | 29.044 | 3700.0 | 44.00 | 2440 | 29.04 |
| Trace Elements | μg/L | nM | μg/L | nM | μg/L | nM | μg/L | nM | μg/L | nM |
| Sodium Selenite | 28.00 | 161.94 | 7.00 | 40.49 | 0.005 | 29.0 | | | 7.00 | 40.49 |
| Fe(NO₃)₃•9H₂O | 49.86 | 123.42 | 49.86 | 123.42 | 0.050 | 124 | 0.10 | 250 | 49.86 | 123.42 |
| CuSO₄ | 2.69 | 16.80 | 0.97 | 6.06 | 0.001 | 5.0 | | | 0.97 | 6.06 |
| CuSO₄•5H₂O | 11.24 | 45.00 | 7.49 | 30.00 | | | | | 7.49 | 30.00 |
| FeSO₄•7H₂O | 2503.85 | 9006.64 | 1542 | 5549 | 0.84 | 3.021 | | | 1542 | 5549 |
| ZnSO₄•7H₂O | 2734.77 | 9528.82 | 1383 | 4821 | 0.430 | 1498 | | | 1383 | 4821 |
| MnSO₄•H₂O | 0.26 | 1.51 | 0.17 | 1.01 | | | | | 0.17 | 1.01 |
| Na2SiO3•9H₂O | 210.00 | 739.27 | 140 | 492.84 | | | | | 140.00 | 492.84 |
| (NH4)₆Mo₇O₂₄•4H₂O | 1.86 | 1.50 | 1.24 | 1.00 | | | | | 1.24 | 1.00 |
| NH₄VO₃ | 0.98 | 8.33 | 0.65 | 5.56 | | | | | 0.65 | 5.56 |
| NiSO₄•6H₂O | 0.20 | 0.74 | 0.13 | 0.49 | | | | | 0.13 | 0.49 |
| SnCl₂•2H₂O | 0.18 | 0.80 | 0.12 | 0.53 | | | | | 0.12 | 0.53 |
| Other Components | mg/L | μM | mg/L | μM | mg/L | μM | mg/L | μM | mg/L | μM |
| Hydrocortisone | 0.23 | 0.64 | .0864 | .24 | 0.036 | 0.0001 | | | 0.09 | 0.24 |
| Putrescine•2HCl | 6.48 | 40.22 | 2.48 | 15.39 | 1.080 | 0.0067 | | | 2.48 | 15.39 |
| linoleic acid | 0.22 | 0.80 | 0.057 | 0.20 | 0.040 | 0.0001 | | | 0.06 | 0.20 |
| thioctic acid | 0.56 | 2.73 | 0.14 | 0.69 | 0.100 | 0.0005 | | | 0.14 | 0.69 |
| D-glucose (Dextrose) | 16039 | 89107 | 11042.24 | 61350 | 8950.7 | 49.7 | 4500.0 | 25000 | 11042 | 61345 |
| PVA | 2560 | | 2520.00 | | 2400.00 | | 2400.0 | | 2520 | 0.00 |
| Nucellin | 54.00 | | 14.00 | | 10.000 | | 10.00 | | 14.00 | 0.00 |
| Sodium Pyruvate | 54.85 | 498.63 | 54.85 | 500 | 54.995 | 500 | 110.0 | 1000 | 54.85 | 498.63 |

In certain embodiments, cells are supplemented at one or more times after the initial culture is begun with one or more feed media. Exemplary feed media are listed in Table 2, although the present invention is not limited to the utilization of these feed media. As will be understood by one of ordinary skill in the art, other feed media may be utilized to grow cells and/or certain alterations may be made to the compositions of the exemplary feed media listed in Table 2. For example, the concentrations of one or more components of such feed media may be increased or decreased to achieve a desired concentration of such components. In certain embodiments, the concentration of each feed medium component is increased or decreased by the same factor. For example, the concentration of each feed medium component may be increased or decreased by 1×, 2×, 3×, 4×, 5×, 6×, 7×, 8×, 9×, 10×, 11×, 12×, 13×, 14×, 15×, 16×, 17×, 18×, 19×, 20×, 25×, 30×, 35×, 40×, 45×, 50× or more.

TABLE 2

Exemplary feed media.

| | Medium F | | Medium G | | Medium H | | Medium I | | Medium J | |
|---|---|---|---|---|---|---|---|---|---|---|
| Amino Acids | mg/L | mM | mg/L | mM | mg/L | mM | mg/L | mM | mg/L | mM |
| alanine | 17.81 | 0.20 | 213.72 | 2.40 | 27.47 | 0.31 | 142.47 | 1.60 | 142.48 | 1.60 |
| arginine | 191.07 | 1.10 | 2292.84 | 13.20 | 1074.21 | 6.17 | 1528.84 | 8.79 | 1528 | 8.79 |
| asparagine•H$_2$O | 270.05 | 1.80 | 3240.60 | 21.60 | 3200.00 | 21.33 | 1080.60 | 7.20 | 1080 | 7.20 |
| aspartic acid | 66.66 | 0.50 | 799.92 | 6.00 | 338.70 | 2.55 | 532.40 | 4.00 | 532.40 | 4.00 |
| cysteine•HCl•H$_2$O | 0.00 | 0.00 | 0.00 | 0.00 | 108.66 | 0.62 | | | 473.00 | 1.51 |
| cysteine•2HCl | 48.83 | 0.16 | 585.96 | 1.92 | 687.50 | 2.20 | 470 | 1.50 | 235.38 | 1.60 |
| glutamic acid | 29.47 | 0.20 | 353.64 | 2.40 | | | 235.38 | 1.60 | 142.48 | 1.60 |
| monosodium glutamate | | | | | 52.17 | 0.31 | | | | |
| glutamine | 456.25 | 3.13 | 5475.00 | 37.56 | | | 6000 | 41.10 | 4820 | 33.01 |
| glycine | 15.01 | 0.20 | 180.12 | 2.40 | 178.26 | 2.38 | 120.07 | 1.60 | 120.07 | 1.60 |
| histidine•HCl•H$_2$O | 73.53 | 0.35 | 882.36 | 4.20 | 732.50 | 3.49 | 588.33 | 2.80 | 588.32 | 2.80 |
| isoleucine | 118.05 | 0.90 | 1416.60 | 10.80 | 880.87 | 6.72 | 944.52 | 7.21 | 944.52 | 7.21 |
| leucine | 170.07 | 1.30 | 2040.84 | 15.60 | 1590.79 | 12.14 | 1360.75 | 10.39 | 1360 | 10.39 |
| lysine•HCl | 182.07 | 1.00 | 2184.84 | 12.00 | 2162.93 | 11.88 | 1456.81 | 8.00 | 1456 | 8.00 |
| methionine | 59.62 | 0.40 | 715.44 | 4.80 | 597.92 | 4.01 | 477.06 | 3.20 | 477.06 | 3.20 |
| phenylalanine | 82.53 | 0.50 | 990.36 | 6.00 | 782.51 | 4.74 | 660.36 | 4.00 | 660.36 | 4.00 |
| proline | 69.03 | 0.60 | 828.36 | 7.20 | 832.67 | 7.24 | 552.31 | 4.80 | 552.31 | 4.80 |
| serine | 158.06 | 1.51 | 1896.72 | 18.12 | 1623.67 | 15.46 | 1264.70 | 12.04 | 1264 | 12.04 |
| threonine | 95.24 | 0.80 | 1142.88 | 9.60 | 871.72 | 7.33 | 762.02 | 6.40 | 762.02 | 6.40 |
| tryptophan | 32.61 | 0.16 | 391.32 | 1.92 | 423.14 | 2.07 | 260.94 | 1.28 | 260.94 | 1.28 |
| tyrosine•2Na•2H$_2$O | 104.26 | 0.40 | 1251.12 | 4.80 | 1100.00 | 4.21 | 832.62 | 3.19 | 832.62 | 3.19 |
| valine | 93.64 | 0.80 | 1123.68 | 9.60 | 1156.01 | 9.88 | 749.21 | 6.40 | 749.21 | 6.40 |
| Vitamins | mg/L | μM | mg/L | μM | mg/L | μM | mg/L | μM | mg/L | μM |
| biotin | 17.81 | 73.00 | 4.92 | 20.16 | 4.14 | 16.96 | 3.28 | 13.44 | 3.28 | 0.01 |
| calcium pantothenate | 191.07 | 401.41 | 54.00 | 113.52 | 33.84 | 71.14 | 36.02 | 75.67 | 36.02 | 0.08 |
| choline chloride | 270.05 | 1943 | 214.92 | 1545 | 244.57 | 1759 | 143.28 | 1030 | 143.28 | 1.03 |
| folic acid | 66.66 | 151.27 | 63.72 | 144.60 | 40.02 | 90.86 | 42.43 | 96.21 | 42.43 | 0.10 |
| inositol | | | 302.52 | 1680 | 253.09 | 1406 | 201.71 | 1120. | 201.71 | 1.12 |
| nicotinamide | 48.83 | 400.41 | 48.00 | 393.60 | 40.48 | 331.93 | 32.018 | 262.44 | 32.02 | 0.26 |
| pyridoxal•HCl | 29.47 | 145.17 | | | 3.13 | 15.42 | | | | |
| pyridoxine•HCl | 456.25 | 2215 | 49.20 | 238.92 | 55.76 | 207.68 | 32.82 | 159.32 | 32.82 | 0.16 |
| riboflavin | 15.01 | 39.92 | 5.40 | 14.40 | 3.73 | 9.92 | 3.60 | 9.57 | 3.60 | 0.01 |
| thiamine•HCl | 73.53 | 218.19 | 92.88 | 275.40 | 100.86 | 299.28 | 35.22 | 104.51 | 35.22 | 0.10 |
| vitamin B12 | 118.05 | 87.12 | 16.80 | 12.36 | 32.67 | 24.11 | 11.21 | 8.27 | 11.21 | 0.01 |
| Inorganic Salts | mg/L | mM | mg/L | mM | mg/L | mM | mg/L | mM | mg/L | mM |
| CaCl$_2$ | | | | | 179.9 | 1.62 | 113.27 | 1.02 | | |
| KCl | | | | | 482.9 | 6.47 | | | | |
| KH$_2$PO$_4$ | | | | | | | 1640 | 12.06 | 1635 | 12.02 |
| Na$_2$HPO$_4$ | | | | | 87.4 | 0.62 | | | | |
| NaCl | | | | | | | | | | |
| NaH$_2$PO$_4$•H$_2$O | 130.50 | 0.95 | 1566.00 | 11.40 | 1496.8 | 10.85 | | | | |
| MgSO$_4$ | | | | | 213.0 | 1.77 | | | | |
| MgSO$_4$•7H$_2$O | 21.50 | 0.09 | 258.00 | 1.08 | | | 170 | 0.690 | 171.98 | 0.70 |
| MgCl$_2$ | | | | | 44.0 | 0.46 | | | | |
| NaHCO$_3$ | | | | | | | | | | |
| Trace Elements | μg/L | nM | μg/L | nM | μg/L | nM | μg/L | nM | μg/L | nM |
| Sodium Selenite | 5.00 | 28.92 | 60.00 | 347.04 | 0.069 | 0.400 | 40 | 231.35 | 40.00 | 231.35 |
| Fe(NO$_3$)$_3$•9H$_2$O | | | | | 0.077 | 0.191 | | | | |
| CuSO$_4$ | 0.43 | 2.69 | 5.16 | 32.28 | 0.016 | 0.099 | 3.44 | 21.51 | 3.44 | 21.51 |
| CuSO$_4$•5H$_2$O | 1.54 | 6.19 | 18.48 | 74.28 | 0.025 | 0.100 | 7.49 | 30.00 | 7.49 | 30.00 |
| FeSO$_4$•7H$_2$O | 571.64 | 2056 | 6859 | 24675 | 7.000 | 25.180 | 2534 | 9115 | 2534 | 9115 |
| ZnSO$_4$•7H$_2$O | 408.08 | 1421 | 4896 | 17062 | 4.075 | 14.199 | 2704 | 9421 | 2704 | 9421 |
| MnSO$_4$•H$_2$O | 0.10 | 0.57 | 1.20 | 6.84 | | | 0.17 | 1.01 | 0.17 | 1.01 |
| Na2SiO3•9H$_2$O | 78.75 | 277.22 | 945.00 | 3326 | | | 140 | 492.84 | 140 | 492.84 |
| (NH$_4$)$_6$Mo$_7$O$_{24}$•4H$_2$O | 0.70 | 0.56 | 8.40 | 6.72 | | | 1.24 | 1.00 | 1.24 | 1.00 |
| NH$_4$VO$_3$ | 0.37 | 3.13 | 4.44 | 37.56 | | | 0.65 | 5.56 | 0.65 | 5.56 |

TABLE 2-continued

Exemplary feed media.

| | Medium F | | Medium G | | Medium H | | Medium I | | Medium J | |
|---|---|---|---|---|---|---|---|---|---|---|
| $NiSO_4 \cdot 6H_2O$ | 0.07 | 0.28 | 0.84 | 3.36 | | | 0.13 | 0.49 | 0.13 | 0.49 |
| $SnCl_2 \cdot 2H_2O$ | 0.07 | 0.30 | 0.84 | 3.60 | | | 0.12 | 0.53 | 0.12 | 0.53 |
| $AlCl3 \cdot 6H_2O$ | | | | | | | 1.2 | 4.97 | 1.20 | 4.97 |
| $AgNO_3$ | | | | | | | 0.17 | 1.00 | 0.17 | 1.00 |
| $Ba(C_2H_3O_2)_2$ | | | | | | | 2.55 | 9.98 | 2.55 | 9.98 |
| KBr | | | | | | | 0.12 | 1.01 | 0.12 | 1.01 |
| $CdCl_2 \cdot 2.5H_2O$ | | | | | | | 2.28 | 9.99 | 2.28 | 9.99 |
| $CoCl_2 \cdot 6H_2O$ | | | | | | | 2.38 | 10.00 | 2.38 | 10.00 |
| $CrCl_3$ | | | | | | | 0.32 | 2.02 | 0.32 | 2.02 |
| NaF | | | | | | | 4.2 | 100.02 | 4.20 | 100.02 |
| $GeO_2$ | | | | | | | 0.53 | 5.07 | 0.53 | 5.07 |
| KI | | | | | | | 0.17 | 1.02 | 0.17 | 1.02 |
| RbCl | | | | | | | 1.21 | 10.01 | 1.21 | 10.01 |
| $ZrOCl_2 \cdot 8H_2O$ | | | | | | | 3.22 | 9.99 | 3.22 | 9.99 |
| Other Components | mg/L | µM | mg/L | µM | mg/L | µM | mg/L | µM | mg/L | µM |
| Hydrocortisone | 0.04 | 0.10 | 0.48 | 1.20 | | | 0.288 | 0.794 | 0.288 | 0.79 |
| Putrescine•2HCl | 1.00 | 6.21 | 12.00 | 74.52 | | | 8 | 49.66 | 8 | 49.66 |
| linoleic acid | 0.04 | 0.15 | 0.48 | 1.80 | | | 0.336 | 1.20 | 0.336 | 1.20 |
| thioctic acid | 0.11 | 0.51 | 1.32 | 6.12 | | | 0.841 | 4.08 | 0.841 | 4.08 |
| D-glucose (Dextrose) | 4194.14 | 23300.80 | 50329 | 279609 | | | 43005 | 238922 | 33005 | 183.37 |
| PVA | 200.00 | | 2400 | | | | 2400 | | 2400 | |
| Nucellin | 10.00 | | 120.00 | | | | 80 | | 80.00 | |
| Sodium Pyruvate | | | | | | | | | | |

Example 2

Small-Scale Investigation of rFIX Peptide Mapping

Introduction: During production of recombinant human blood clotting Factor IX ("rFIX") bulk drug substance ("BDS"), a batch to batch difference was observed in the relative peak area ratio ("RPAR") of the K4 peptide within the peptide map. The samples were prepared by digestion with lysyl endopeptidase from Achromobacter lyticus ("AchroK", Wako catalog #129-02541), and subsequent resolution by reverse-phase HPLC. The RPAR of the K4 peptide fell below the lower limit of 82% of the control sample of the reference material in certain batches and reached a minimum of 78% of the control sample. The balance of the material was found in the K4' peak. The difference between the two peaks is entirely due to the extent of glycosylation at Ser-61. The K4 species has a Sia-α2,3-Gal-β1,4-GlcNAc-β1,3-Fuc-α1-O tetrasaccharide linked to the serine, while the K4' species that increased proportionally has just fucose.

A full scale cell culture experiment was run during a period when the peptide map differences were occurring. Cells were grown in a cell culture medium that was supplemented with $FeSO_4$, $CUSO_4$ and choline chloride to 2x, 7x and 2x, respectively. BDS produced by small-scale purification of the experimental batches showed improved K4 RPAR, but control material purified in the same way did not. The BDS lots passed the peptide map requirements (≧82% of control sample), although they did not reach the level seen in the reference material. This indicated that the difference observed in the RPAR maps is a result of the cell culture process and might be related to a nutrient deficiency.

In-Process Sample Analyses: The cells were removed from the cell culture medium by microfiltration ("MF") and ultrafiltration/diafiltration ("UF/DF") steps, resulting in fairly pure material from individual bioreactors that was available for analysis.

To investigate whether or not the K4 species is being degraded back to the K4' (fucose-only) species after secretion from the cell, a modified analysis was performed on an in-process sample from the UF/DF retentate. A large sample of the retentate was split into three equal aliquots. One was purified immediately over a small-scale capture column; this served as a negative control. The other two were each incubated overnight at 37° C. prior to being purified in a similar manner. One of the overnight aliquots had sialidase added to remove the terminal sialic acid from the K4 species in case the sialic acid was blocking the activity of some other glycosidase. After the small-scale purification, all three samples were analyzed for K4 species as above. FIG. 1 shows that there was no degradation in any sample beyond that catalyzed by the sialidase. This was a very strong indication that the peptide map problem was anabolic, meaning that the "missing" sugar residues at Ser-61 were never added to the nascent chain. It remained possible, although it is extremely unlikely, that the glycosidic activity responsible for removing those sugar residues was inactivated or removed by the MF and UF/DF steps. The results also demonstrated the utility of the small-scale purification system for analyzing samples from upstream of the Q Sepharose step.

Small-scale modeling: Small-scale rFIX cultures grown in shake flasks were used as a model to evaluate the effects of various media and additives on the K4 species. In each case, the conditioned medium from the shake flasks was purified directly (without UF/DF) over a small-scale capture column using volume-based peak collection and the K4 distribution in the sample was determined.

The utility of the small-scale model was demonstrated using the same additives as in the full scale experiment. Manganese additions were also analyzed, since a literature search found that $Mn^{++}$ is required for similar glycosylation activity of a fruitfly enzyme (see Moloney et al., *J. Biol. Chem.* 275(13): 9604-9611, 2000; Bruckner et al., *Nature* 406: 411-415, 2000). The comparisons were carried out over four passages in the shake flasks, and the results are shown in FIG. 2. Duplicate injections for each sample are shown. "P#" indicates the passage number of each condition. For P1-2, the concentration of Mn was 1 nM; for P3-4, it was 10 nM. The difference between the control and the supplemented medium K4 species distributions is comparable to the difference seen in the production bioreactors. Differences are manifested after a single passage and multiple passages do not reveal any trends.

Since the additives included three components ($FeSO_4$, $CUSO_4$ and choline chloride), the next experiment addressed which of these components was responsible for the improved K4 species distribution. The three components were added to three rFIX shake flask cultures. The components were added pair-wise to reveal any synergistic effects. Other cultures included positive (all three components) and negative (no additives) controls.

FIG. 3 shows that $FeSO_4$ was the additive that was responsible for helping improve the K4 species distribution. Duplicate injections for each sample are shown. Additions were at the experimental concentrations. It appears that addition of $CuSO_4$ and choline chloride, in the absence of $FeSO_4$, may even make the distribution worse. It should be noted that, for unknown reasons, the de-sialylated form of K4' started showing up in greater abundance in both the test samples and the assay reference. This trend is apparent in FIG. 3 and continues in subsequent experiments.

Inductively-coupled plasmaspectroscopy ("ICP") analysis of the iron content of the medium powder demonstrated that the proper quantity of iron was present in the powder. This led to the hypothesis that the benefit derived from the added $FeSO_4$ is actually caused by a trace contaminant of that raw material. The $FeSO_4$ lot that was used in the original medium conditions was analyzed by ICP analysis, and several trace impurities showed up at levels above the limit of detection. By eliminating known inhibitors and components of the rFIX cell culture medium, the list was narrowed to the following nine potentially beneficial elements: Sb, Bi, B, Co, Ge, Mn, Mo, Ni, and V.

Next, small-scale modeling experiments were conducted to explore some other possible additives that might complement the original medium additives. Additional $CuSO_4$, $ZnSO_4$ and $MnSO_4$ (to 10 nM) were tested. The $ZnSO_4$ was included because zinc can competitively inhibit the uptake of other divalent cations. For unknown reasons, the control and experimental conditions gave very similar K4 species distributions that were more like what had previously been observed for the control conditions (see FIG. 4, duplicate injections for each sample are shown). However, the addition of $MnSO_4$ to the experimental condition clearly improved the K4 species distribution. It appears that the added $ZnSO_4$ may have worsened the K4 species distribution, but the significance of that difference is not certain.

It was noted above that an increase in the level of the de-sialylated K4' peak was observed in FIG. 3. This phenomenon continued and trended up over the course of the described small-scale studies. This trend does not change the interpretation of the results as presented.

Conclusion: Extensive testing of in-process and small-scale capture column eluates has provided strong evidence that a difference in the medium powder caused the shift in the K4 RPAR, which in turn led to the multiple peptide map differences. Because adding certain components to the cell culture medium reversed the shift, in part, it was likely that the difference in the medium powder is that one or more components shifted to lower levels. Since the most effective additive discovered was $FeSO_4$, and ICP analysis showed that the medium powder contained the appropriate amount of Fe, it was therefore hypothesized that a trace impurity in the $FeSO_4$ is necessary for proper glycosylation at Ser-61. Based on the ICP analysis of the $FeSO_4$, the trace impurity was not a specified component of the medium powder, but rather was an incidental nutrient that had previously always been present in the medium.

Example 3

Small-scale Studies of the Impact of Medium Additives on the rFIX Peptide Map

Introduction: Example 2 demonstrated that batch to batch differences in the extent of glycosylation at Ser-61 were observed in various rFIX batches, which is seen as a shift in the K4 peptide population distribution. All rFIX batches have a distribution of chain lengths at this site dominated by the full-length tetrasaccharide (Sia-α2,3-Gal-β1,4-GlcNAc-β1, 3-Fuc-al), but some batches had an unusually high fraction of the fucose-only form.

Example 2 also demonstrated that the shift in the K4 distribution occurred in the bioreactor and was tightly linked to a lot change of the medium powder. The results of Example 2 lend strong support to the hypothesis that the change in glycoform distribution was an anabolic function, not a catabolic one. Furthermore, these experiments demonstrated that supplemental $FeSO_4$ could partially reverse the shift, but ICP analysis showed that there was no significant difference in the $FeSO_4$ concentration between the medium powder lots. Thus, it was hypothesized that another, unidentified trace component of the $FeSO_4$ that was present at varying levels with the different medium powder lots was responsible for the shift.

Additive Effects: As discussed in Example 2, ICP analysis showed measurable quantities of nine trace elements in the $FeSO_4$ lot used for the experimental culture conditions. A comparison of these trace elements against those in published medium formulations eliminated the need to add Sb or Bi. Based on the medium formulations and ICP analysis of the $FeSO_4$, a mix of five compounds was created to add to the rFIX cultures (final medium concentrations given): 1 nM $(NH_4)_6Mo_7O_{24}$, 10 nM $CoCl_2$, 5.5 nM $NH_4VO_3$, 1.5 nM $NiSO_4$, and 20 nM $H_3BO_3$. $MnSO_4$ was added separately since an earlier literature review had indicated that manganese might be important for glycosyltransferase activity (see Breton and Imberty, *Curr. Opinion in Structural Biol.* 9: 563-571, 1999; Bruckner et al., *Nature* 406: 411-415, 2000). In the same experiment, additional $FeSO_4$ (2× or 4×) was tested to determine whether it could further increase the relative amount of the tetrasaccharide. In each case, the additives were used in addition to the supplements described in Example 2.

The results of this addition experiment are shown in FIG. 5. Species distributions were determined and the values reported are the ratios of the area of each of the four K4 peak to their sum. The figure also shows a reference material, the control (no additive) and the supplemented (as in Example 2) cultures. Duplicate injections for each sample are shown. In each set of columns, the leftmost column corresponds to the fraction of molecules with a tetrasaccharide at Ser-61, and the rightmost column is the fraction with only a fucose. The observed difference between the positive and negative control cultures (supplemented and not supplemented, respectively) was smaller than had been seen previously. Regardless, FIG. 5 clearly demonstrates that the mix of trace elements had no effect on the K4 species distribution, while the addition of $FeSO_4$ and $MnSO_4$ both improved the K4 species distribution. When added to the supplements, 15 nM $MnSO_4$ had approximately the same effect on the K4 species distribution an additional 12 μM $FeSO_4$.

The strong response to manganese led to experiments designed to find an optimum concentration for the manganese in the rFIX cell culture medium. FIG. 6 shows that this experiment gave results consistent with those shown in FIG. 5, as all of the cultures with added manganese had less fucose-only K4 than did the either the supplemented or the control culture. In fact, cultures with 40 nM or more manganese had about the same amount of fucose-only K4 as did the assay reference material. However, there appeared to be more of the trisaccharide at 100 or 500 nM than at 40 nM manganese. Thus, it was determined that 40 nM was an unexpectedly advantageous manganese concentration for more extensive FIX glycosylation at Ser-61.

Utility of the Small-Scale Model: One unusual feature of these small-scale experiments, and those presented in Example 2, was the varying level of the trisaccharide, or de-sialated species, from experiment to experiment. Because this species varies similarly to the assay reference, it is believed to be an artifact of the single-pot digestion method. Since all samples for a given experiment were digested at the same time using the same raw material, this variability is not believed to impact the analyses presented in this Example or in Example 2.

Conclusion: These experiments demonstrated that the addition of 40 nM $MnSO_4$ to the rFIX cell culture medium improves the K4 species distribution.

Example 4

N-Linked Oligosaccharide Analysis of Anti-ABeta Culture Medium Samples

Introduction: The N-linked oligosaccharide fingerprints of CHO cells expressing a humanized anti-ABeta peptide IgG1 monoclonal antibody ("anti-ABeta cells") were investigated under four media conditions. The sample identifications and relevant information are listed in Table 3.

TABLE 3

Anti-ABeta samples harvested from various culture conditions.

| Sample ID | Condition | Gln | Trace E | Vol (mL) | Day | Concentration |
|---|---|---|---|---|---|---|
| 1 |  | High | No | 1 | 14 | 3.06 mg/mL |
| 2 | Trace E | High | Yes | 1 | 14 | 4.61 mg/mL |
| 3 | Low Gln (4 mM) Trace E | Low | Yes | 1 | 14 | 4.44 mg/mL |
| 4 | Low Gln (4 mM) 2 g/L Glu | Low | No | 1 | 14 | 4.14 mg/mL |

Procedure: Anti-ABeta culture 1 was grown and fed periodically with feed medium. In anti-ABeta culture 2, Trace Elements E were added at the outset. Table 4 lists the composition of Trace Elements E. Anti-ABeta culture 3 was grown in conditions identical to culture 2 except that the initial glutamine level was 4 mM. Anti-ABeta culture 4 was grown in conditions identical to culture 3 except that no Trace E was added and the feed medium was supplemented with glutamate to 2 g/L.

Glycoform distributions of each sample were determined by PNGase F digestion, followed by High pH Anionic Exchange Chromatography with Pulsed Electrochemical Detection (HPAEC-PED) analysis. Briefly, samples were buffer exchanged into 50 mM ammonium formiate, buffered at pH 7.3, using Amicon Ultra 30,000 MWCO protein concentrators. After recovery, each sample was digested with 5 µL PNGase F (glycerol free) and incubated overnight at 37° C. The samples were then dried down by speed vacuum centrifugation and reconstituted in purified water. Samples were then transferred to autosampler vials for HPAEC-PED analysis. The HPAEC-PED system is equipped with a Dionex CarboPac PA100 guard and analytical column (2×250 mm), and an ED-40 detector. A linear gradient of sodium acetate was used which includes two eluents: Eluent A which consists of 100 mM NaOH and Eluent B which consists of 100 mM NaOH/500 mM sodium acetate.

TABLE 4

Composition of Trace Elements E.

| Trace Elements E | µg/L | nM |
|---|---|---|
| $(NH_4)6Mo_7O_{24} \cdot 4H_2O$ | 123.60 | 100.00 |
| $AlCl_3 \cdot 6H_2O$ | 0.48 | 2.00 |
| $H_3BO_3$ | 6.18 | 100.00 |
| $CrCl_3$ | 7.92 | 50.00 |
| $CuSO_4 \cdot 5H_2O$ | 49.94 | 200.00 |
| $GeO_2$ | 0.21 | 2.00 |
| KBr | 0.24 | 2.00 |
| KI | 16.60 | 100.00 |
| LiCl | 0.08 | 2.00 |
| $MnSO_4 \cdot H_2O$ | 16.90 | 100.00 |
| $Na_2SiO_3 \cdot 9H_2O$ | 142.03 | 500.00 |
| NaF | 0.08 | 2.00 |
| $NH_4VO_3$ | 1.17 | 10.00 |
| $NiSO_4 \cdot 6H_2O$ | 2.63 | 10.00 |
| RbCl | 0.24 | 2.00 |
| $SnCl_2 \cdot H_2O$ | 0.45 | 2.00 |
| Sodium Selenite | 34.58 | 200.00 |

Data Analysis: The three types of complex N-linked biantennary glycans that are associated with the anti-ABeta antibody contain zero ("G0"), one ("G1") or two (G2") galactose residues on their outer N-linked biantennary arms. All samples showed the presence of the three peaks representative of G0, G1, and G2 glycoforms. FIG. 7 shows a graphical comparison of percentage of total peak area for the G0, G1, and G2 HPAEC-PED peaks of each sample. The presence of additional small peaks was observed in the profiles of all submitted samples. The observed peaks represent low levels of mono- and di-sialylated glycoforms.

Discussion: These experiments tested the relative distribution of G0:G1:G2 peaks of anti-ABeta cultures supplemented with feed media under various experimental conditions. Cultures in which Trace Elements E were added demonstrated a drop in G0 levels, with a corresponding increase in G1 and G2 levels relative to culture conditions that lacked Trace Elements E (FIG. 7). Culture conditions that contained low glutamine had a similar effect, and the effects were additive. Low glutamine (4 mM) cultures in which Trace Elements E were added demonstrated a dramatic shift in the distribution of N-link glycoforms, with nearly equal proportions of G0 and G1 and with G2 representing approximately 10% of total peak area (FIG. 7). Cultures to which Trace Elements E was added contained manganese at a concentration of 156 nM. However, it should be noted that the cultures also contained elevated levels of other metals. Thus, it is possible that, in addition to manganese, other culture conditions contributed to the improved glycosylation pattern observed.

Conclusion: Differences in the glycosylation distributions observed in the anti-ABeta samples are most likely due to respective changes in culture conditions. Our data strongly suggest that the presence of low glutamine (4 mM) and/or the addition of Trace Element E containing 100 mM $MnSO_4$ results in a dramatic change in the percentage distribution the various N-linked glycoforms in anti-ABeta. These effects appear to be independent and additive.

Example 5

N-Linked Oligosaccharide Analysis of Anti-ABeta Manganese Study Samples

Introduction: Example 4 demonstrated that improvements in glycosylation distributions of anti-ABeta samples could be attained by the addition of Trace Elements E to the culture conditions and by keeping glutamine levels low. Here we tested whether addition of manganese alone in the culture conditions could effect a similar improvement in glycoslyation distributions.

Procedure: Anti-ABeta cultures were grown in culture media either containing or lacking 40 mM manganese. The cultures were fed with 40% total volume of feed media. Samples were harvested and analyzed according to the method described in Example 4.

Data Analysis: The analyzed samples were compared in terms of peak presence and percentage of total peak area for each peak. FIG. 8 shows a graphical comparison of percentage of total peak area for the G0, G1, and G2 HPAEC-PED peaks of each sample.

Discussion: The three types of complex N-linked biantennary glycans that are associated with the anti-ABeta antibody are the G0, G1, and G2 structures, which respectively contain zero, one or two galactose residues on their outer N-linked biantennary arms. Samples harvested from cells grown in media either lacking or containing 40 mM manganese showed the presence of all three peaks representative of G0, G1, and G2 glycoforms. The G0 peak decreased from 68% total peak area in the control sample to 53% in the sample harvested from media containing added manganese (see FIG. 8). Increases in G1 and G2 percentages of total peak area were also seen in the sample harvested from media containing manganese. The G1 percentages of total peak area were 26% in the control sample, and 39% in the manganese-added sample. The G2 percentages of total peak area were 6% in the control sample and 9% in the manganese-added sample (FIG. 8).

Conclusion: These data indicate that the addition of manganese alone to the culture medium results in a more extensive glycosylation pattern as demonstrated by a shift in the percentage distribution of G0:G1:G2 in these samples.

We claim:

1. A method of producing a glycoprotein in a cell culture comprising:
    culturing mammalian cells that contain a gene encoding a glycoprotein of interest in a cell culture medium comprising between approximately 10 nM and 600 nM manganese, wherein the glycoprotein of interest comprises O-linked oligosaccharide chains;
    maintaining the culture at a first temperature range of about 30 to 42 degrees Celsius for a first period of time sufficient to allow the cells to reproduce to a viable cell density within a range of about 20%-80% of the maximal possible viable cell density if the culture were maintained at the first temperature range; and
    shifting the culture to a second temperature range and maintaining the culture for a second period of time sufficient to permit expression of the glycoprotein, wherein the second temperature range comprises a temperature range that is approximately 25 to 41 degrees Celsius, wherein the glycosylation pattern of the expressed glycoprotein is more extensive than the glycosylation pattern observed under otherwise identical conditions in otherwise identical medium that lacks the manganese.

2. The method of claim 1, wherein the first temperature range comprises a temperature that is approximately 37 degrees Celsius.

3. The method of claim 1, wherein the second temperature range comprises a temperature that is approximately 31 degrees Celsius.

4. The method of claim 1, wherein the cell culture medium comprises between approximately 20 and 200 nM manganese.

5. The method of claim 4, wherein the cell culture medium comprises approximately 40 nM manganese.

6. The method of claim 1, wherein the cell culture medium comprises glutamine at an initial concentration which is less than or equal to approximately 8 mM.

7. The method of claim 6, wherein the initial glutamine concentration of the cell culture medium is less than or equal to approximately 4 mM.

8. The method of claim 1, wherein the volume of the cell culture is about 500 L.

9. The method of claim 1, wherein the cell culture is further provided with a feed medium after the initial cell culture is begun.

10. The method of claim 1, wherein the cell culture is further provided with supplementary components.

11. The method of claim 10 wherein the supplementary components are selected from the group consisting of hormones and/or other growth factors, inorganic ions, buffers, vitamins, nucleosides or nucleotides, trace elements, amino acids, lipids, glucose or other energy sources, and combinations thereof.

12. The method of claim 11, wherein the cell culture is supplemented with approximately 2 grams per liter glucose.

13. The method of claim 1, wherein the cell culture medium is defined.

14. The method of claim 1, wherein the glycoprotein of interest comprises coagulation factor IX.

15. The method of claim 14, wherein the coagulation factor IX is recombinant human coagulation Factor IX.

16. A method of producing a glycoprotein in a cell culture comprising steps of:
    culturing mammalian cells that contain a gene encoding coagulation Factor IX (FIX) as a glycoprotein of interest in a cell culture medium comprising approximately 40 nM manganese under conditions and for a time sufficient to permit expression of the FIX glycoprotein, wherein the glycosylation pattern of the expressed FIX glycoprotein is more extensive at 40 nM manganese than the FIX glycosylation pattern observed at other manganese levels under otherwise identical conditions in otherwise identical medium.

17. A method of producing a glycoprotein in a cell culture comprising steps of:
    culturing mammalian cells that contain a gene encoding coagulation Factor IX (FIX) as a glycoprotein of interest in a cell culture medium comprising 10 nM-600 nM manganese under conditions and for a time sufficient to permit expression of the FIX glycoprotein, wherein the glycosylation pattern of the expressed FIX glycoprotein is more extensive at 10 nM-600 nM manganese than the FIX glycosylation pattern observed at other manganese levels under otherwise identical conditions in otherwise identical medium.

18. A method of producing a glycoprotein in a cell culture comprising:
    culturing mammalian cells that contain a gene encoding a glycoprotein of interest in a cell culture medium comprising between approximately 10 nM and 600 nM manganese, wherein the cell culture medium comprises glutamine at an initial concentration which is less than or equal to approximately 8 mM, and wherein the glycoprotein of interest comprises O-linked oligosaccharide chains;

maintaining the culture at a first temperature range of about 30 to 42 degrees Celsius for a first period of time sufficient to allow the cells to reproduce to a viable cell density within a range of about 20%-80% of the maximal possible viable cell density if the culture were maintained at the first temperature range; and maintaining the culture for a second period of time sufficient to permit expression of the glycoprotein, wherein the glycosylation pattern of the expressed glycoprotein is more extensive than the glycosylation pattern observed under otherwise identical conditions in otherwise identical medium that lacks the manganese.

* * * * *